US012584143B2

(12) United States Patent
Mirzadeh et al.

(10) Patent No.: US 12,584,143 B2
(45) Date of Patent: Mar. 24, 2026

(54) COMBINATION OF TIS SEQUENCE AND SIGNAL PEPTIDE SEQUENCE FOR EXPRESSING A RECOMBINANT PROTEIN

(71) Applicant: XBRANE BIOPHARMA AB, Solna (SE)

(72) Inventors: Kiavash Mirzadeh, Solna (SE); Veronica Ramberg, Ekero (SE); Nathalie Chatzissavidou, Sodertalje (SE); Patrik Samuelson, Saltsjobaden (SE); Siavash Bashiri, Stockholm (SE); Per Edebrink, Stockholm (SE); Joanne Stevenson, Sodertalje (SE); David Vikstrom, Upplands Vasby (SE)

(73) Assignee: XBRANE BIOPHARMA AB, Solna (SE)

( * ) Notice: Subject to any disclaimer, the term of this patent is extended or adjusted under 35 U.S.C. 154(b) by 758 days.

(21) Appl. No.: 17/911,772

(22) PCT Filed: Mar. 17, 2021

(86) PCT No.: PCT/SE2021/050233
§ 371 (c)(1),
(2) Date: Sep. 15, 2022

(87) PCT Pub. No.: WO2021/188034
PCT Pub. Date: Sep. 23, 2021

(65) Prior Publication Data
US 2023/0175008 A1      Jun. 8, 2023

(30) Foreign Application Priority Data

Mar. 17, 2020    (SE) .................................... 2030080-2
Mar. 17, 2020    (SE) .................................... 2030082-8
Mar. 17, 2020    (SE) .................................... 2030083-6
Mar. 17, 2020    (SE) .................................... 2030084-4
Mar. 17, 2020    (SE) .................................... 2030085-1
Mar. 17, 2020    (SE) .................................... 2030086-9

(51) Int. Cl.
*C12N 15/85*        (2006.01)
*C07K 16/28*        (2006.01)

(52) U.S. Cl.
CPC .......... *C12N 15/85* (2013.01); *C07K 16/2818* (2013.01); *C12N 2830/34* (2013.01)

(58) Field of Classification Search
None
See application file for complete search history.

(56) References Cited

FOREIGN PATENT DOCUMENTS

| | | |
|---|---|---|
| CN | 104854133 B | 8/2015 |
| CN | 110366429 B | 10/2019 |
| EP | 2 906 599 B1 | 8/2015 |
| WO | 2014058389 A1 | 4/2014 |
| WO | 2018/158332 A1 | 9/2018 |

OTHER PUBLICATIONS

Kober, et al. Optimized signal peptides for the development of high expressing CHO cell lines. Biotechnology and Bioengineering. Apr. 2013; v110(4):1164-73. (Year: 2013).*
Petersen, et al. Modular 5'-UTR hexamers for context-independent tuning of protein expression in eukaryotes. Nucleic Acids Research. Aug. 2018; v46(21)1-11. (Year: 2018).*
Human Genome Variation Society. Nomenclature for the description of sequence variants: codons and amino acids. Oct. 2009. (Year: 2009).*
Haryadi R. et al., "Optimization of Heavy Chain and Light Chain Signal Peptides for High Level Expression of Therapeutic Antibodies in CHO Cells", PLoS ONE 10(2):e0116878 (Feb. 23, 2015).
Kober L. et al., "Optimized Signal Peptides for the Development of High Expressing CHO Cell Lines", Biotechnology and Bioengineering 110(4):1164-1173 (Apr. 2013).
International Search Report dated Apr. 26, 2021 issued in PCT/SE2021/050233.
Petersen, S D et al., "Modular 5'-UTR hexamers for context-independent tuning of protein expression in eukaryotes", Nucleic Acids Research (2018), vol. 46, No. 21, e127, pp. 1-11.
You, Min et al., "Efficient mAB production in CHO cells with optimized signal peptide, codon and UTR", Applied Microbiology and Biotechnology (2018), vol. 102, pp. 5953-5964.
Li, Yan-Mei et al., "Construction strategies for developing expression vectors for recombinant monoclonal antibody production in CHO cells", Molecular Biology Reports (2018), vol. 45, pp. 2907-2912.

* cited by examiner

*Primary Examiner* — Allison M Fox
*Assistant Examiner* — Gina Pronzati
(74) *Attorney, Agent, or Firm* — Scully, Scott, Murphy & Presser, P.C.

(57) ABSTRACT

The present invention relates to DNA constructs comprising a novel TIS sequence. The TIS sequence transcribes into an RNA motif that functions as the protein translation initiation site in an mRNA transcript. The DNA construct may further comprise a nucleic acid sequence encoding signal peptide. Additionally, the DNA constructs may also comprise a nucleic acid sequence encoding a recombinant protein or one or more polypeptide chains thereof. The invention further relates to an expression vector, expression cassette and host cell which comprise said DNA constructs. Furthermore, the present invention relates to a recombinant protein expressed by the host cell as well as a method for expressing the recombinant protein.

25 Claims, 7 Drawing Sheets

Specification includes a Sequence Listing.

COMBINATION OF TIS SEQUENCE AND SIGNAL PEPTIDE SEQUENCE FOR EXPRESSING A RECOMBINANT PROTEIN

TECHNICAL FIELD

The present invention relates to DNA constructs comprising a novel TIS sequence. The DNA construct may also comprise a nucleic acid sequence encoding signal peptide. Additionally, the DNA constructs may also comprise a nucleic acid sequence encoding a recombinant protein or one or more polypeptide chains thereof. The invention further relates to an expression vector, expression cassette and host cell which comprise said DNA constructs. Furthermore, the present invention relates to a recombinant protein expressed by the host cell as well as a method for expressing the recombinant protein.

INCORPORATION BY REFERENCE OF SEQUENCE LISTING

The Sequence Listing in an ASCII text file, named as 41292_Sequence_Listing.txt of 22 KB, created on Sep. 14, 2022, and submitted to the United States Patent and Trademark Office via EFS-Web, is incorporated herein by reference.

BACKGROUND OF INVENTION

The major determinants for the steady state protein concentration levels in recombinant cell lines involve (1) the genomic integration site of the expression cassette, (2) promoter strength, (3) translation efficiency of the transcript and (4) protein folding and post translational modifications affecting degradation rates. For generation of recombinant Chinese hamster ovary (CHO) cell lines, often random integration sites that facilitate high expression levels are screened through. The expression vector itself also contains regulatory elements such as a promoter sequence that yields high transcription and a translation initiation site (TIS) that enables proper translation initiation [1]. Frustratingly, even though all regulatory elements that ought to facilitate high expression levels are selected for, protein yields can differ in a context dependent manner. A solution that would guide in the rational design when generating a recombinant cell line is therefore highly sought-after.

Since protein synthesis uses up a large fraction of the cell's energy budget [2], evolution has tightly regulated the different phases of protein production. The eukaryotic translation initiation phase requires twelve initiation factors and is believed to be the rate-limiting step during protein synthesis [3]. This initiation phase has most likely become tightly regulated during evolution to minimize energy consumption. The major element regulating the efficiency of translation initiation is embedded in the mRNA nucleotide sequence surrounding the ATG start codon. This nucleotide bias within the TIS was discovered in the 1980's and is commonly known as the Kozak sequence [4]. Ribosomal structural studies have since then elucidated how the TIS sequence interacts with the ribosome, imposing conformational changes for translation initiation to occur [5]. Due to their biological impact, TIS sequences with different strengths have naturally evolved as indicators for true initiation sites and for fine tuning expression levels [6].

Usually, a strong naturally occurring TIS sequence is selected for when engineering the expression vector for recombinant production. Among other TIS variants, the mammalian consensus sequence GCCACC preceding the ATG start codon [7] is routinely introduced during ad hoc construct design. This sequence is prevalent for naturally found highly expressed genes, likely resulting in enhanced fitness of the organism by fine tuning translation initiation rates for abundant transcripts. In contrast to natural evolution, fed-batch recombinant expression conditions alter the proteome and impose a metabolic burden on cells that by no means mimic natural circumstances [8]. Consequently, recent studies have focused on experimentally screening through TIS libraries in order to identify common sequence features that lead to optimal translation rates for recombinant experiments [9, 10].

However, prior art does not suggest one unique universal sequence that could be reliably used. Consequently, there is a need for TIS sequences that could provide better technical effects than the GCCACCATG sequence.

Moreover, mammalian cells are commonly used as hosts for production of recombinant biopharmaceuticals. Cell lines derived from Chinese hamster ovary (CHO) cells can routinely allow for production yields in the g/L range. However, despite advances in the field, expression levels can vary in an unpredictable and context dependent manner, limiting the rational design for obtaining a desired expression level during cell line development. In order to solve this problem, the translation initiation site (TIS) has been altered in the present invention with the aim of ultimately influencing the titer and productivity of antibodies.

THE OBJECT OF THE INVENTION

The object of the invention is to increase translation initiation rates.

A further object of the invention is to increase translation initiation rates without effecting protein quality.

A further object of the invention is to increase translation initiation rates whilst maintaining protein biosimilarity.

A further object of the invention is to increase translation initiation rates whilst maintaining post translational modifications.

A further object of the invention is to increase translation initiation rates whilst maintaining glycan-based post translational modifications.

A further object of the invention is to increase translation initiation rates whilst maintaining acidic and basic distribution of species.

A further object of the invention is to increase expression of recombinant proteins.

A further object of the invention is to increase titer of recombinant proteins.

A further object of the invention is to increase titer of antibodies or fragments thereof.

A further object of the invention is to increase titer of monoclonal antibodies.

SUMMARY OF INVENTION

The objects of the invention are attained by the subject-matter disclosed in the claims as well as the subject-matter disclosed in the below aspects of the invention.

A first aspect of the invention relates to a DNA construct suitable for expressing a recombinant protein in mammalian cells, wherein the DNA construct comprises a nucleic acid sequence of SEQ ID No 1, wherein the nucleic acid sequence of SEQ ID No 1 is a TIS sequence.

In a preferred embodiment, the nucleic acid sequence of SEQ ID No 1 comprises:

6 nucleotides upstream of an ATG start codon; and/or 2 nucleotides downstream of an ATG start codon.

In a preferred embodiment, the DNA construct further comprises a nucleic acid sequence which encodes a signal peptide.

In a preferred embodiment, the DNA construct further comprises a nucleic acid sequence which encodes a recombinant protein or one or more polypeptide chains thereof.

A second aspect of the invention to relates to a DNA construct for expressing a recombinant protein in mammalian cells, wherein the DNA construct comprises:

a nucleic acid sequence of SEQ ID No 1, wherein the nucleic acid sequence of SEQ ID 1 is a TIS sequence; and a nucleic acid sequence which encodes a signal peptide.

In a preferred embodiment, the nucleic acid sequence of SEQ ID No 1 comprises:

6 nucleotides upstream of an ATG start codon; and/or 2 nucleotides downstream of an ATG start codon.

In a preferred embodiment, the nucleic acid sequence which encodes a signal peptide comprises a nucleic acid sequence of SEQ ID No 2.

In a preferred embodiment, the nucleic acid sequence of SEQ ID No 1 comprises:

the ATG start codon in the nucleic acid sequence which encodes the first amino acid residue of the signal peptide; and the first two nucleotides downstream of the ATG start codon in the nucleic acid sequence which encodes the second amino acid residue of the signal peptide.

In a preferred embodiment, the nucleic acid sequence of SEQ ID No 1 comprises:

the ATG start codon in SEQ ID No 2; and the first two nucleotides downstream of the ATG start codon in the nucleic acid sequence of SEQ ID No 2.

A third aspect of the invention to relates to a DNA construct for expressing a recombinant protein in mammalian cells, wherein the DNA construct comprises:

a nucleic acid sequence of SEQ ID No 1, wherein the nucleic acid sequence of SEQ ID 1 is a TIS sequence;

a nucleic acid sequence which encodes a signal peptide; and a nucleic acid sequence which encodes for a recombinant protein, preferably a monoclonal antibody, more preferably an IgG4 monoclonal antibody.

In a preferred embodiment, the nucleic acid sequence of SEQ ID No 1 comprises:

6 nucleotides upstream of an ATG start codon; and/or 2 nucleotides downstream of an ATG start codon.

In a preferred embodiment, the nucleic acid sequence which encodes a signal peptide comprises a nucleic acid sequence of SEQ ID No 2.

In a preferred embodiment, the nucleic acid sequence of SEQ ID No 1 comprises:

the ATG start codon in the nucleic acid sequence which encodes the first amino acid residue of the signal peptide; and the first two nucleotides downstream of the ATG start codon in the nucleic acid sequence which encodes the second amino acid residue of the signal peptide.

In a preferred embodiment, the nucleic acid sequence of SEQ ID No 1 comprises:

the ATG start codon in SEQ ID No 2; and the first two nucleotides downstream of the ATG start codon in the nucleic acid sequence of SEQ ID No 2.

In a preferred embodiment, the nucleic acid sequence which encodes the signal peptide is operably linked to the nucleic acid sequence which encodes for the recombinant protein.

A fourth aspect of the invention relates to a DNA construct for expressing a recombinant protein in mammalian cells, wherein the DNA construct comprises:

a first and second nucleic acid sequences each comprising a nucleic acid sequence of SEQ ID No 1, wherein the nucleic acid sequence of SEQ ID 1 is a TIS sequence;

a first nucleic acid sequence which encodes a signal peptide;

a second nucleic acid sequence which encodes a signal peptide;

a first nucleic acid sequence which encodes a heavy chain of an antibody; and a second nucleic acid sequence which encodes a light chain of an antibody.

In a preferred embodiment, a nucleic acid sequence of SEQ ID No 1 comprises:

6 nucleotides upstream of an ATG start codon; and/or 2 nucleotides downstream of an ATG start codon.

In a preferred embodiment, a nucleic acid sequence which encodes a signal peptide comprises a nucleic acid sequence of SEQ ID No 2.

In a preferred embodiment, the first and second nucleic acid sequences which encode a signal peptide each comprise a nucleic acid sequence of SEQ ID No 2.

In a preferred embodiment, the first and second nucleic acid sequences each comprising a nucleic acid sequence of SEQ ID No 1 comprise:

the ATG start codon in the first and second nucleic acid sequences which encode the first amino acid residue of the signal peptide; and the first two nucleotides downstream of the ATG start codon in the first and second nucleic acid sequences which encode the second amino acid residue of the signal peptide.

In a preferred embodiment, the first and second nucleic acid sequences comprising a nucleic acid sequence of SEQ ID No 1 comprise:

the ATG start codon in SEQ ID No 2 of the first and second nucleic acid sequences which encode a signal peptide, and the first two nucleotides downstream of the ATG start codon in SEQ ID No 2 of the first and second nucleic acid sequences which encode a signal peptide.

In a preferred embodiment, the first nucleic acid sequence which encodes a signal peptide is operably linked to the first nucleic acid sequence which encodes the heavy chain of an antibody.

In a preferred embodiment, the second nucleic acid sequence which encodes a signal peptide is operably linked to the second nucleic acid sequence which encodes the light chain of an antibody.

In a preferred embodiment, the first nucleic acid sequence which encodes the heavy chain of an antibody encodes an amino acid sequence of SEQ ID No 5.

In a preferred embodiment, the second nucleic acid sequence which encodes the light chain of an antibody encodes an amino acid sequence of SEQ ID No 7.

In a preferred embodiment, the first and second nucleic acid sequences which encode for the heavy and light chains of an antibody, respectively, encode an amino acid sequence of SEQ ID No 5 and SEQ ID No 7, respectively.

In a preferred embodiment, the first nucleic acid sequence which encodes the heavy chain of an antibody comprises a sequence of SEQ ID No 4.

In a preferred embodiment, the second nucleic acid sequence which encodes for the light chain of an antibody comprises a sequence of SEQ ID No 6.

In a preferred embodiment, the first and second nucleic acid sequence which encode the heavy and light chains of an antibody, respectively, comprise a sequence of SEQ ID No 4 and SEQ ID No 6, respectively.

In a preferred embodiment, the DNA construct comprises nucleic acid sequences of SEQ ID No 8 and SEQ ID No 9. The resulting heavy and light chains of an antibody may each comprise a cleaved or an uncleaved signal peptide. In the case when the signal peptides are not cleaved, each of said heavy and light chains having an uncleaved signal peptide comprises an amino acid sequence of SEQ ID No 10 and SEQ ID No11, respectively.

In a preferred embodiment, the DNA construct comprises nucleic acid sequences of SEQ ID No 12 and SEQ ID No 13. The resulting heavy and light chains of an antibody may each comprise a cleaved or an uncleaved signal peptide. In the case when the signal peptides are not cleaved, each of said heavy and light chains having an uncleaved signal peptide comprises an amino acid sequence of SEQ ID No 10 and SEQ ID No11, respectively.

A fifth aspect of the invention relates to a DNA construct comprising a nucleic acid sequence encoding an amino acid sequence, wherein the amino acid sequence comprises:

the amino acid sequence for Nivolumab (Opdivo, CAS number 946414-94-4);

a signal peptide of SEQ ID No 3 fused to the heavy chain amino acid sequence of Nivolumab; and a signal peptide of SEQ ID NO 3 fused to the light chain amino acid sequence of Nivolumab.

In a preferred embodiment, the heavy chain amino acid sequence of Nivolumab comprises a sequence of SEQ ID No 5.

In a preferred embodiment, the light chain amino acid sequence of Nivolumab comprises a sequence of SEQ ID No 7.

In a sixth aspect of the invention relates to an expression vector which comprises the DNA construct according to the any one of the first to fifth aspects of the invention.

In a preferred embodiment, the expression vector comprises one or more of the following nucleic acid elements:

promoter, terminator, selection marker, origin of replication, and/or antibiotic resistance marker, wherein the expression vector further comprises at least one multiple cloning site cleavable by a restriction enzyme, preferably the restriction enzyme is EcoRI, NdeI, NotI, XhoI, PspXI, PaeR71, BbsI, StyI, AvrII, BanI, Acc65I, KpnI, Eco53kI, SacI, BamHI, XbaI, SalI, AccI, PstI, SbfI, SphI or HindIII.

In a preferred embodiment, the selection marker comprises the gene encoding dihydrofolate reductase, DHFR, or glutamine synthetase, GS.

A seventh aspect of the invention relates to an expression cassette which comprises the DNA construct according to the any one of the first to fifth aspects of the invention.

An eighth aspect of the invention relates to a host cell which comprises a DNA construct according to any one of the first to fifth aspects of the invention, wherein said host cell is preferable and eukaryotic cell, more preferably a mammalian cell.

In a preferred embodiment, the host cell is a Chinese hamster ovary, CHO, cell.

In a preferred embodiment, the host cell is a CHO-DG44 cell or a CHO GS$^{-/-}$ cell.

A ninth aspect of the invention relates to a recombinant protein expressed by a DNA construct according to any one of the first to fifth aspects of the invention. The recombinant protein may comprise one or more polypeptide chains.

In a preferred embodiment, the recombinant protein is an antibody, antibody fragment, enzyme and hormone.

In a preferred embodiment, the recombinant protein is monoclonal antibody, polyclonal antibody, chimeric antibody or a fragment of said monoclonal antibody, polyclonal antibody, chimeric antibody.

In a preferred embodiment, the recombinant protein is Nivolumab. Nivolumab is a human IgG4 monoclonal antibody. It is a therapeutic antibody which is sold under the brand name Opdivo and is a medication used to treat a number of types of cancer. This includes melanoma, lung cancer, renal cell carcinoma, Hodgkin lymphoma, head and neck cancer, colon cancer, and liver cancer. It is typically used by slow injection into a vein.

A tenth aspect of the invention relates to RNA expressed by the DNA construct according to any one of the first to fifth aspects of the invention.

An eleventh aspect of the invention relates to a method of expressing a recombinant protein, comprising the steps of:

a. cloning one or more open reading frames encoding a recombinant protein, or one or more polypeptide chains thereof, into one or more DNA constructs according to any one of the first to third aspects of the invention; and b. transfecting the resulting nucleic acid sequences into a host cell, wherein the host cell is preferably a eukaryotic cell, more preferably a mammalian cell.

In a preferred embodiment, the method further comprises the step of integrating the transfected nucleic acid sequence into the genome of the host cell.

A thirteenth aspect of the invention relates to a method of expressing a recombinant protein, comprising the steps of:

a. cloning a DNA construct according to the fourth or fifth aspects of the invention; and b. transfecting the resulting nucleic acid sequences into a host cell, wherein the host cell is preferably a eukaryotic cell, more preferably a mammalian cell.

In a preferred embodiment, the method further comprises the step of integrating the transfected nucleic acid sequence into the genome of the host cell.

A fourteenth aspect of the invention relates to a DNA construct for expressing a signal peptide in any type of host cell (including prokaryotic cell, eukaryotic cell and/or yeast cell), wherein the DNA construct comprises a nucleic acid sequence which encodes a signal peptide, wherein the nucleic acid sequence which encodes a signal peptide comprises a nucleic acid sequence of SEQ ID No 2. The nucleic acid sequence of SEQ ID No 2 encodes a signal peptide comprising an amino acid sequence of SEQ ID No 3. Further aspects relate to an expression vector, expression cassette and host cell which comprise said DNA construct.

Figure 2:
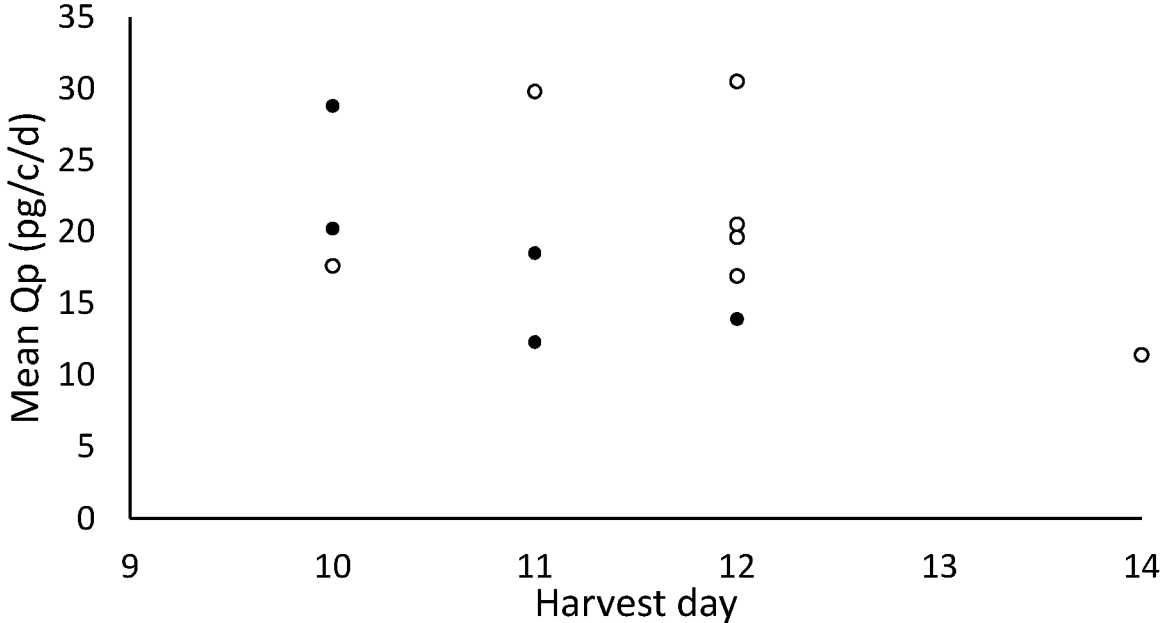

FIG. 2—Increased likelihood of identifying high antibody producing cell cultures for mini-pools containing a TIS$^{EVO}$-chart represents mean productivity, mean Qp, (pg/c/d) on harvest day for mini-pools containing a TIS$^{CON}$ (black) or TIS$^{EVO}$ (hallow).

Figure 3:
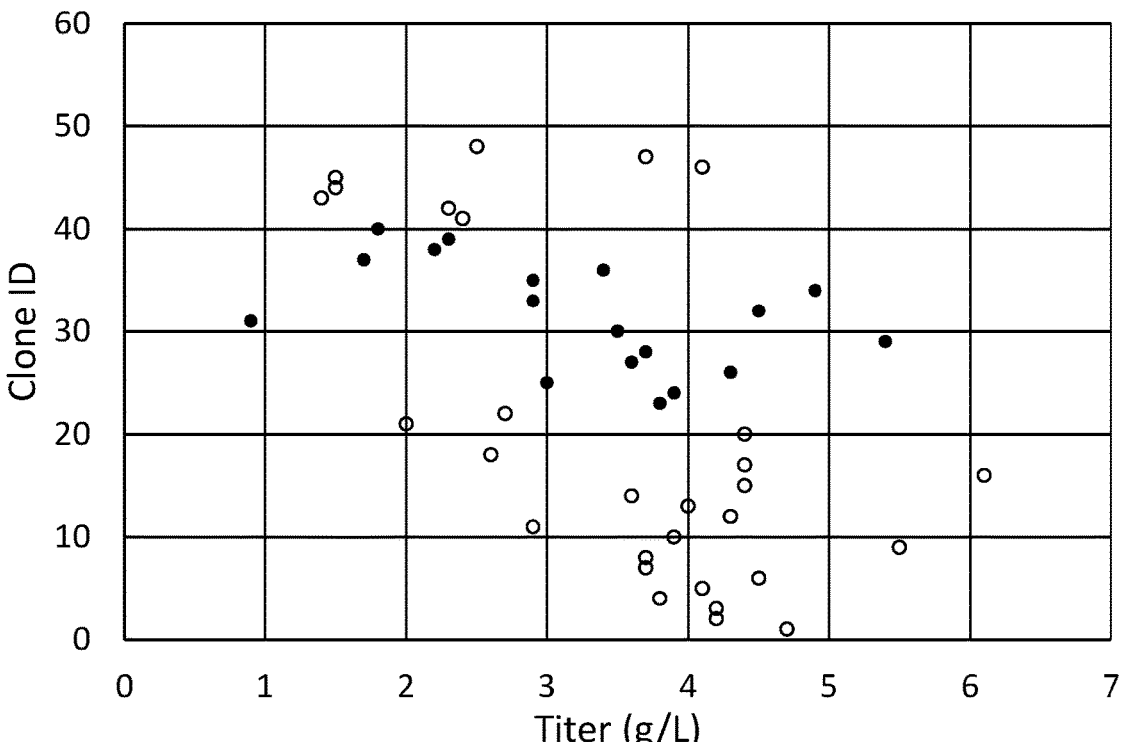

FIG. 3—Titer and specific productivity comparison of monoclonal antibody (mAb) expressing CHO-DG44 cell lines-Final accumulated titer values (g/L) of cell lines harboring a TIS$^{CON}$ (black dots) or TIS$^{EVO}$ (hollow dots).

Figure 4:
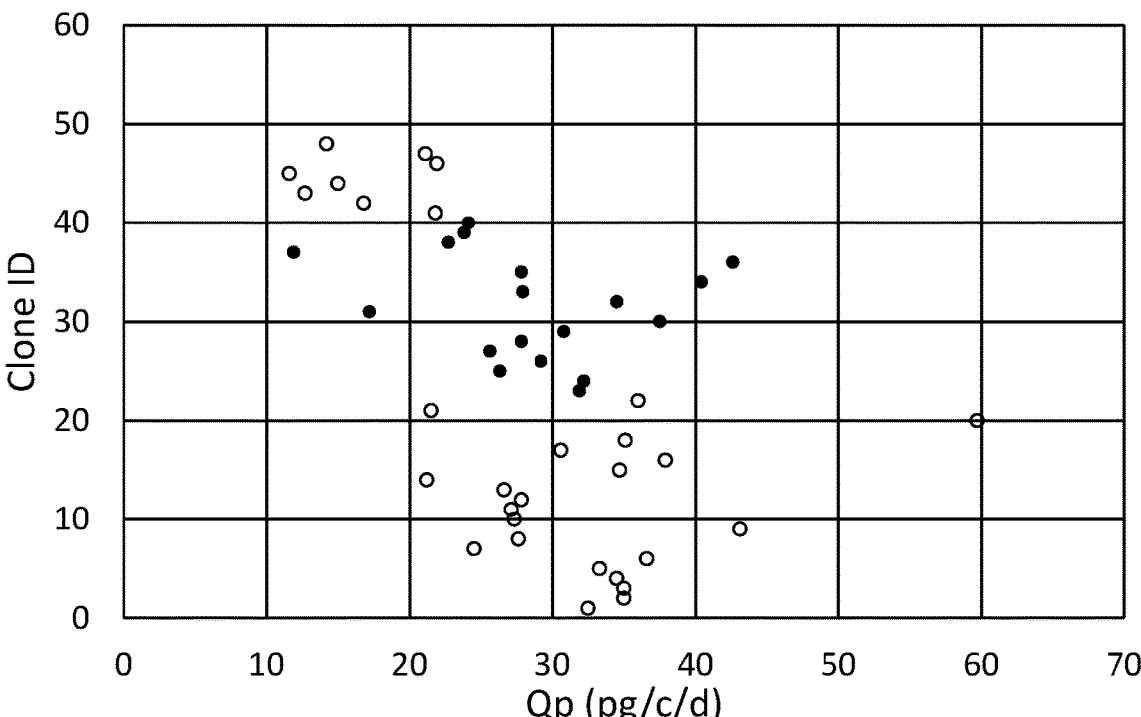

FIG. 4—Titer and specific productivity comparison of mAb expressing CHO-DG44 cell lines-Final accumulated specific productivity, Qp, (pg/c/d) of cell lines harboring a TIS$^{CON}$ (black dots) or TIS$^{EVO}$ (hollow dots).

Figure 5:
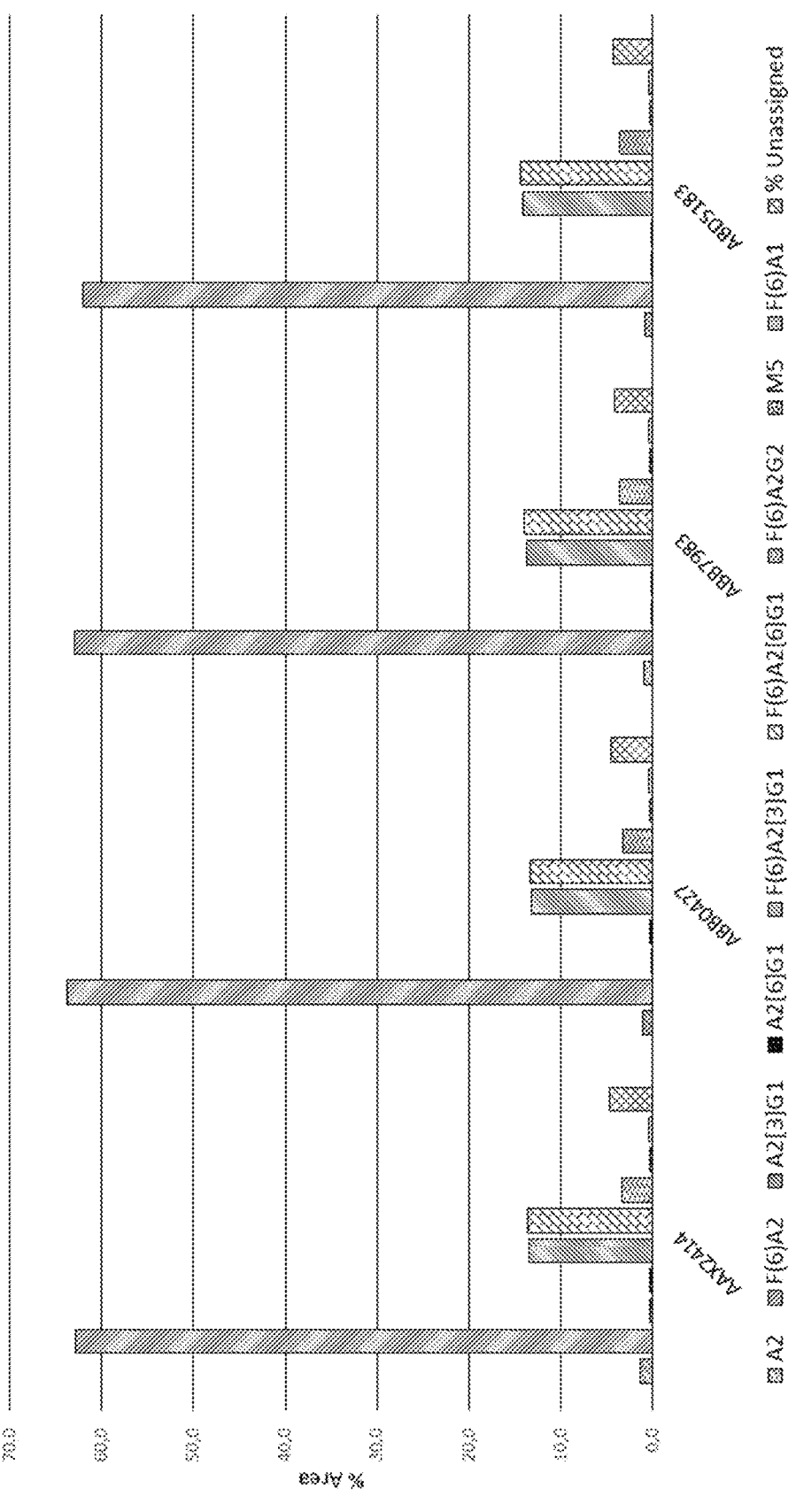

FIG. 5—Glycan profile of commercially obtained Nivolumab (i.e. these samples have been produced without the use of TIS$^{CON}$ and TIS$^{EVO}$).

Figure 6:
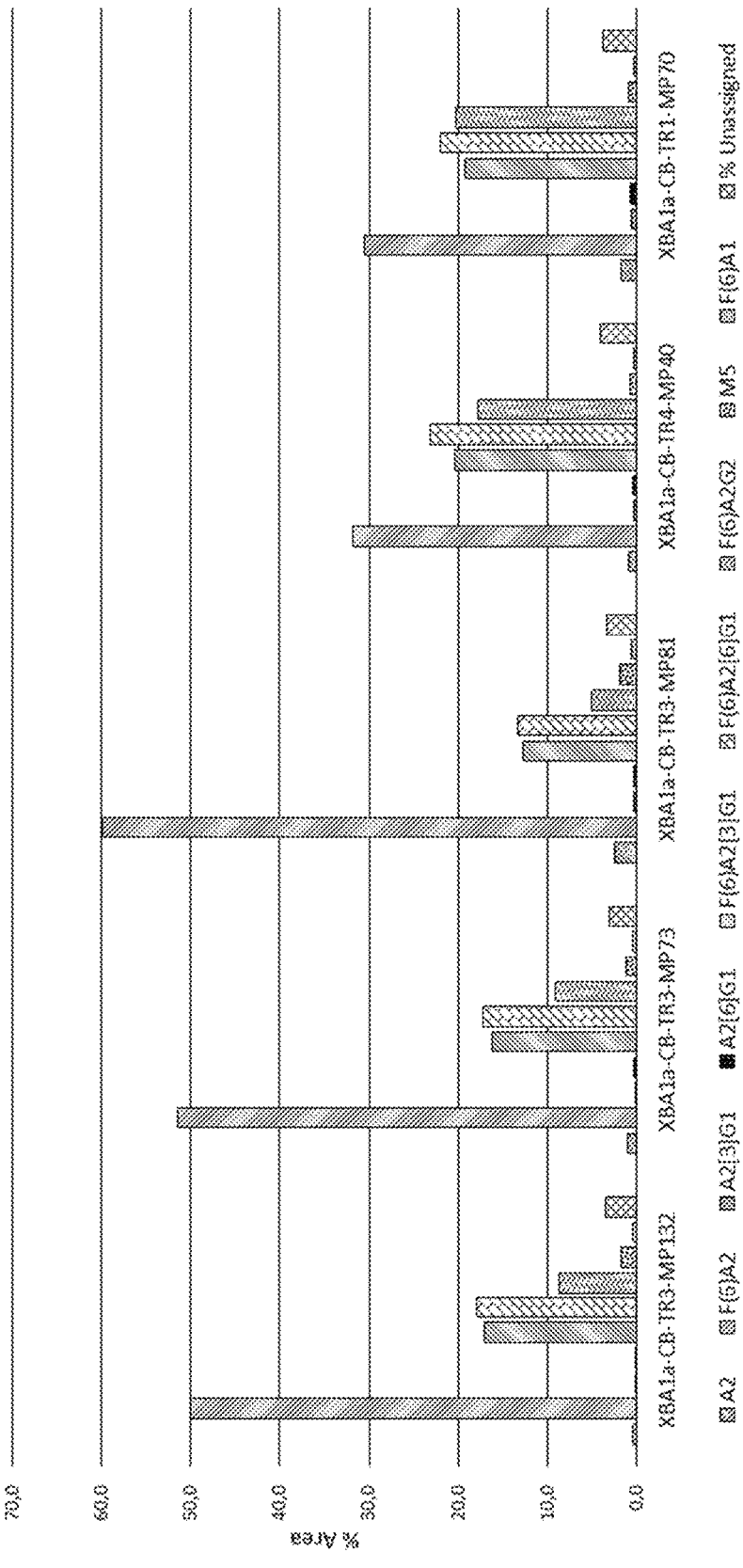

FIG. 6—Glycan profile of Nivolumab variants derived from TIS$^{CON}$ containing mini pools.

Figure 7:
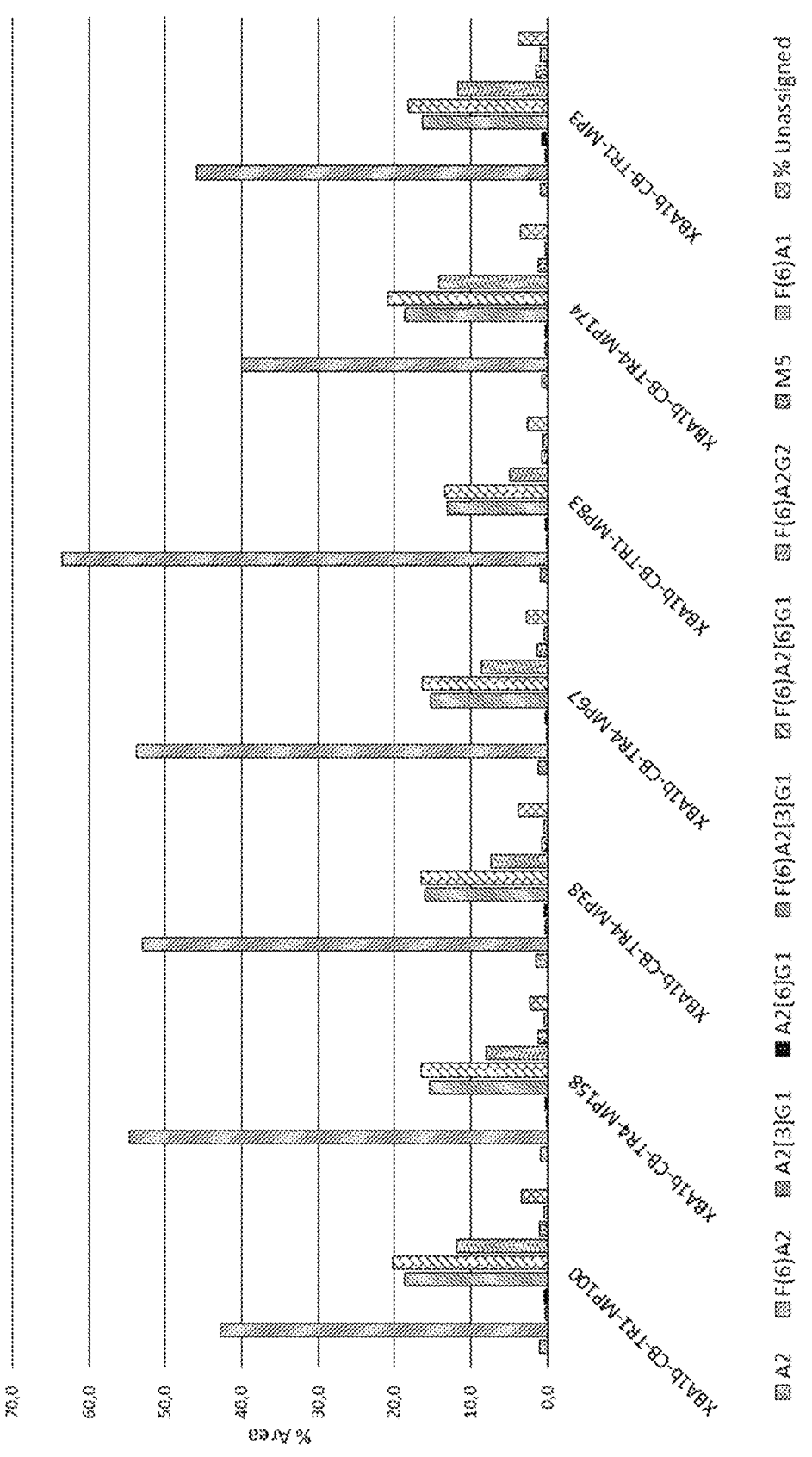

FIG. 7—Glycan profile of Nivolumab variants derived from TIS$^{EVO}$ containing mini pools.

Figure 8:
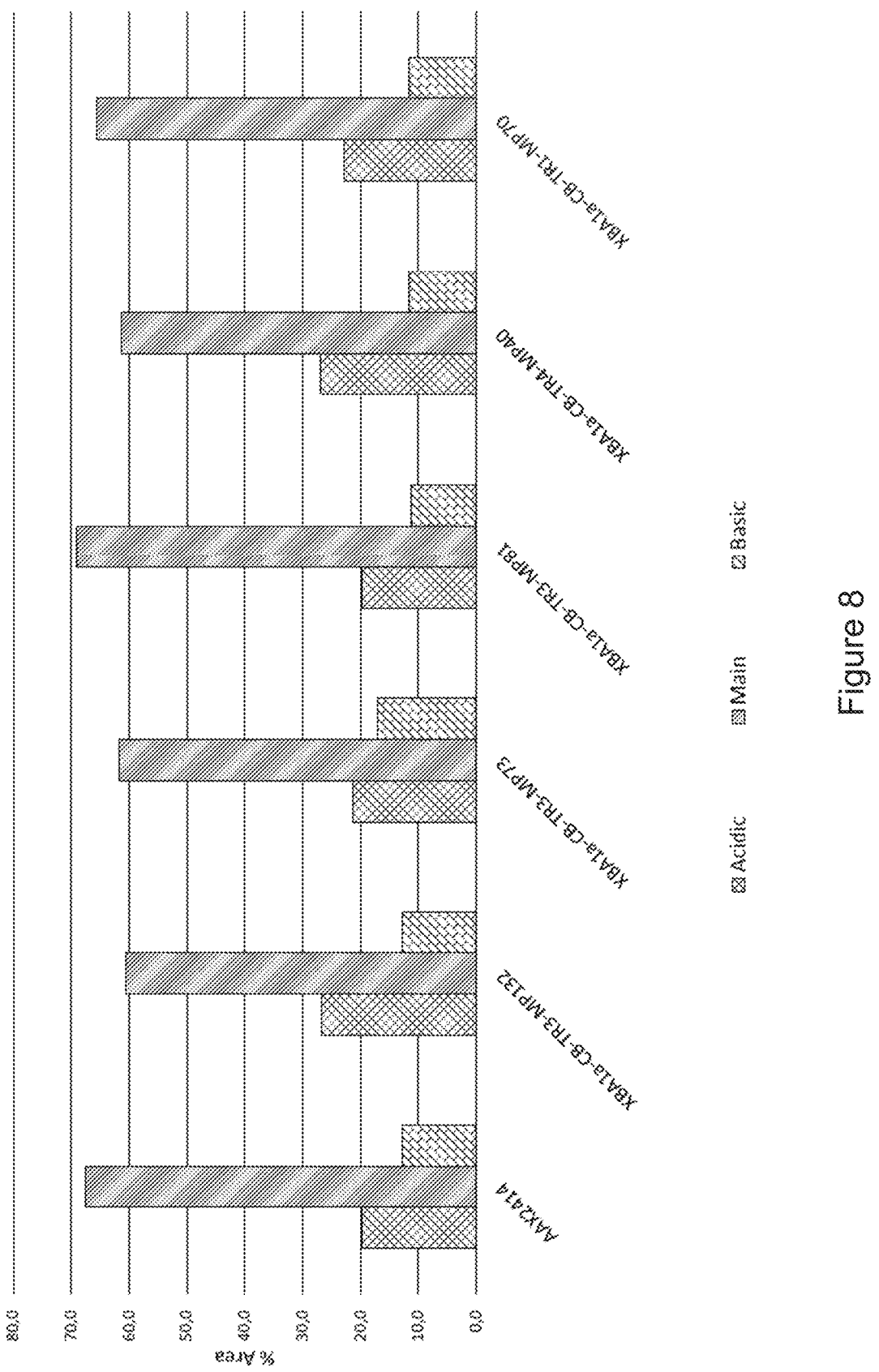

FIG. 8—Charge distribution of Nivolumab variants derived from TIS$^{CON}$ mini pools. The originator is labeled AAX2414.

Figure 9:
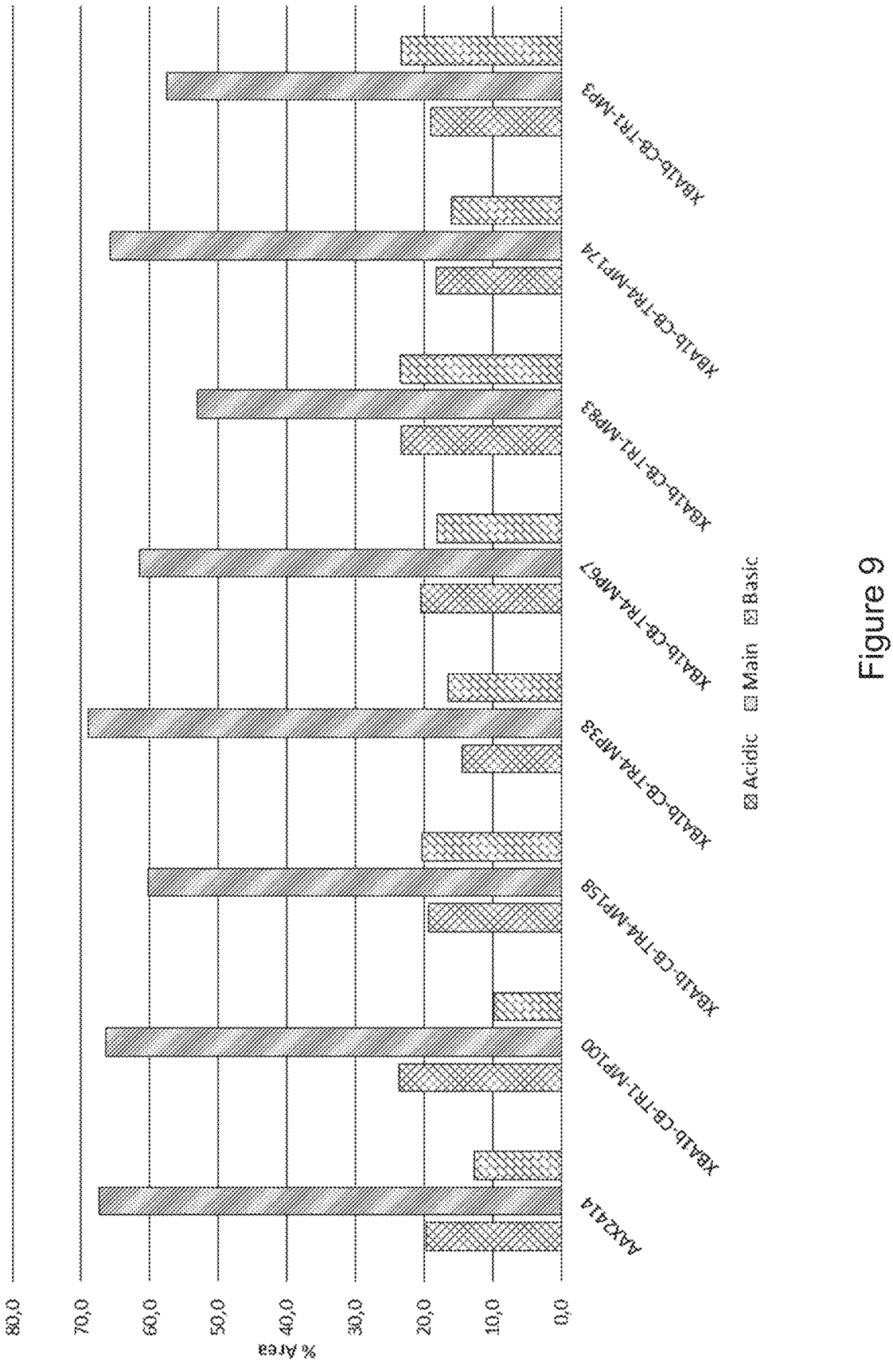

FIG. 9—Charge distribution of Nivolumab variants derived from TIS$^{EVO}$ mini pools. The originator is labeled AAX2414.

DETAILED DESCRIPTION

In the art, a TIS sequence is sometimes referred to as the RNA sequence that functions as the protein translation initiation site (TIS) in an mRNA transcript [9]. However, in the present invention, the term TIS sequence instead refers to the DNA sequence which transcribes into said RNA sequence.

Since prior art studies do not suggest one unique universal sequence that could be reliably used, the inventor has designed a novel nucleic acid TIS sequence (herein referred to as TIS$^{EVO}$) that provides better technical effect than the prior art GCCACCATGGA sequence (herein labelled TIS$^{CON}$) in a recombinant expression system for producing an antibody in mammalian cells.

The novel TIS sequence herein referred to as TIS$^{EVO}$ comprises the nucleic acid sequence of TCGGTCATGGC which is also referred to as SEQ ID No 1 in the present invention.

In the present invention, the term nucleic acid means at least two nucleotides covalently linked together. Moreover, the disclosure of a single strand also discloses the sequence of the complementary strand. Thus, a nucleic acid sequence also encompasses the complementary strand of a disclosed single strand.

The nucleic acid sequence of SEQ ID No 1 is comprised in a DNA construct which is suitable for expressing a recombinant protein in mammalian cells. The TIS$^{EVO}$ nucleic acid sequence of SEQ ID No 1 comprises:

6 nucleotides (immediately) upstream of the ATG start codon (i.e. comprises nucleotides from position −6 to −1 in which the A of the ATG start codon is position +1), as well as 2 nucleotides (immediately) downstream of the ATG start codon (i.e. comprises nucleotides from position +4 to +5 in which the G of the ATG start codon is position +3)

In the present invention, the term DNA construct means refers to an artificially constructed segment of nucleic acid that is to be inserted into a host cell (e.g. via using an expression vector or expression cassette).

The TIS$^{EVO}$ nucleic acid sequence transcribes into an RNA sequence of UCGGUCAUGGC (herein also referred to as SEQ ID No 14) that functions as the protein translation initiation site in an mRNA transcript. In other words, the TIS$^{EVO}$ nucleic sequence is a Kozak-like sequence.

The above mentioned DNA construct may further comprise a nucleic acid sequence which encodes a signal peptide. The nucleic acid sequence of SEQ ID No 1 may in such a DNA construct comprise:

the ATG start codon in the nucleic acid sequence which encodes the first amino acid residue of the signal peptide; and the first two nucleotides downstream of the ATG start codon in the nucleic acid sequence which encodes the second amino acid residue of the signal peptide.

In the present invention, the term signal peptide refers to a leader peptide which is fused to the N-terminus of the recombinant protein to be expressed. Signal peptides facilitate secretion of the recombinant protein from the host cell in which it is produced. Signal peptides are typically cleaved from the remainder of the upon secretion from the cell.

In an embodiment of the invention, the nucleic acid sequence which encodes the signal peptide according to the present invention comprises a modification of the nucleic acid sequence which expresses a signal peptide having methionine (M) as the first amino acid at the N-terminus end of the signal peptide. Such signals peptides may be selected from as the ones described in Kober et al [11], Haryadi R. et al [12], U.S. Pat. No. 10,066,019, Ramezani A. et al [15] and Peng L. et al [16] which all relate to use of signal peptides for expression of recombinant proteins in eukaryotic host cells. The modification according to the present invention involves a change of the first codon downstream of the ATG start codon by exchanging the first two nucleotides to GC. The resulting signal peptide will comprise MA as the first two amino acids at the N-terminus end of the signal peptide.

In an embodiment of the invention, the nucleic acid sequence which encodes the signal peptide comprises a nucleic acid sequence of SEQ ID No 2. The nucleic acid sequence of SEQ ID No 1 will in such a DNA construct comprise:

the ATG start codon in SEQ ID No 2; and the first two nucleotides downstream of the ATG start codon in the nucleic acid sequence of SEQ ID No 2.

The DNA construct may further comprise a nucleic acid sequence which encodes a recombinant protein. In such as DNA construct, the nucleic acid sequence which encodes the signal peptide may be operably linked to the nucleic acid sequence which encodes the recombinant protein. The recombinant protein may be an antibody, a multimeric protein, a monomeric protein, enzyme and/or hormone. However, other recombinant proteins may also be envisaged.

The term antibody is in the present invention referred to a monoclonal antibody, polyclonal antibody, chimeric antibody or a fragment thereof. Such a fragment of an antibody (herein also refer to as antibody fragment) is a portion of an intact antibody comprising the antigen-binding site or variable region. An antibody fragment may be a Fab fragment, Fab' fragment, Fab'-SH fragment, F(ab') 2 fragment, Fd fragment, Fv fragment, diabody, triabody and/or single-chain Fv (scFv) molecule.

In an embodiment of the invention, the DNA construct comprises:

two nucleic acid sequence of SEQ ID No 1;

two nucleic acid sequences which encode signal peptides; and a recombinant protein;

wherein the nucleic acid sequences which encode the signal peptides may be the same or different sequences, i.e. the signal peptides may be the same or different signal peptides. The construction of vectors which express signal peptides which are same or different are known in the art as described in Kober et al [11], Haryadi R. et al [12] and Li F. et al [13]. The recombinant protein is preferably an antibody. Moreover, each of the nucleic acid sequences which encode signal peptide is operably linked to two nucleic acid sequences (such as nucleic acid sequences encoding the heavy and light chains) of the recombinant proteins.

In an embodiment of the invention, the DNA construct comprises:

a first and second nucleic acid sequences each comprising a nucleic acid sequence of SEQ ID No 1, a first nucleic acid sequence which encodes a signal peptide;

a second nucleic acid sequence which encodes a signal peptide;

a first nucleic acid sequence which encodes a heavy chain of an antibody; and a second nucleic acid sequence which encodes a light chain of an antibody.

In such as DNA construct, the first and second nucleic acid sequences of SEQ ID No 1 comprise:

the ATG start codon in the first and second nucleic acid sequences which encode the signal peptides; and the first two nucleotides downstream of the ATG start codon in the first and second nucleic acid sequences which encode the signal peptides.

The first nucleic acid sequence which encodes a signal peptide is operably linked to the first nucleic acid sequence which encodes the heavy chain of an antibody. Similarly, the second nucleic acid sequence which encodes a signal peptide is operably linked to the second nucleic acid sequence which encodes the light chain of an antibody.

In an embodiment of the invention, the DNA construct of the first and second nucleic acid sequences which encode the signal peptides may each comprise a nucleic acid sequence of SEQ ID No 2. In such a DNA construct, the first and second nucleic acid sequences of SEQ ID No 1 comprise:

the ATG start codon in SEQ ID No 2 of the first and second nucleic acid sequences which encode the signal peptides, the first two nucleotides downstream of the ATG start codon in SEQ ID No 2 of the first and second nucleic acid sequences which encode the signal peptides.

The first nucleic acid sequence which encodes the heavy chain of an antibody may encode an amino acid sequence of SEQ ID No 5. The second nucleic acid sequence which encodes the light chain of an antibody may encode an amino acid sequence of SEQ ID No 7.

The first nucleic acid sequence which encodes the heavy chain of an antibody may comprise a nucleic acid sequence of SEQ ID No 4. The second nucleic acid sequence which encodes for the light chain of an antibody may comprise a nucleic acid sequence of SEQ ID No 6.

The DNA construct may comprise a nucleic acid sequence of SEQ ID No 8 or SEQ ID No 12 wherein said sequence comprises:

a first nucleic acid sequence comprising a nucleic acid sequence of SEQ ID No 1;

a first nucleic acid sequence which encodes a signal peptide comprising a nucleic acid sequence of SEQ ID No 2; and a first nucleic acid sequence which encodes a heavy chain of an antibody comprising a nucleic acid sequence of SEQ ID No 4;

wherein the first nucleic acid sequences of SEQ ID No 1 comprises:

the ATG start codon in SEQ ID No 2 of the first nucleic acid sequence which encodes a signal peptide; and the first two nucleotides downstream of said ATG start codon.

The DNA construct may comprise a nucleic acid sequence of SEQ ID No 9 or SEQ ID No 13 wherein said sequence comprises:

a second nucleic acid sequence comprising a nucleic acid sequence of SEQ ID No 1;

a second nucleic acid sequence which encodes a signal peptide comprising a nucleic acid sequence of SEQ ID No 2; and a second nucleic acid sequence which encodes a light chain of an antibody comprising a nucleic acid sequence of SEQ ID No 6, wherein the second nucleic acid sequences of SEQ ID No 1 comprises:

the ATG start codon in SEQ ID No 2 of the second nucleic acid sequence which encodes a signal peptide; and the first two nucleotides downstream of said ATG start codon.

The DNA construct may comprise both of nucleic acid sequences of SEQ ID No 8 and SEQ ID No 9. Alternatively, the DNA construct may instead comprise both of the nucleic acid sequences of SEQ ID No 12 and SEQ ID No 13. Nucleic acids of SEQ ID No 12 and 13 differ from nucleic acids of SEQ ID No 8 and 9, respectively, only in that nucleic acid of SEQ ID No 12 and 13 each further comprise restriction sites.

The above disclosed DNA construct may be integrated into an expression vector suitable for transfecting into mammalian cells. Such a vector may comprise the following nucleic acid elements:

promoter, terminator, selection marker, origin of replication, and/or antibiotic resistance marker.

The expression vector may further comprise at least one multiple cloning site cleavable by a restriction enzyme such as EcoRI, NdeI, NotI, XhoI, PspXI, PaeR71, BbsI, StyI, AvrII, BanI, Acc65I, KpnI, Eco53kI, SacI, BamHI, XbaI, SalI, AccI, PstI, SbfI, SphI and/or HindIII.

Expression vector for use with mammalian cells as well as nucleic acid elements which are typically comprised in such expression vectors are described in Li F. et al [13] and Noh S. H. et al [14] and the uses of these expression vectors in the present invention are indicated in the below described embodiments of the expression vector.

The expression vector may include one or more promoters. The promoter may be any promoter that is capable of driving gene expression and regulating gene expression. Preferably, the promoter may be a promoter shown effective for expression of recombinant proteins in mammalian cells such as CHO cells. In a further preferred embodiment, the promoter is effective for expression of recombinant proteins in CHO-DG44 cells. A specific example of a promoter which may be used in the present invention is a cytomegalovirus (CMV) promoter and/or elongation factor alpha (EF1α) promoter.

In expression vectors having a DNA construct comprising:
  a first nucleic acid sequence which encodes a heavy chain of an antibody,
  a second nucleic acid sequence which encodes a light chain of an antibody,
the expression vector may comprise a first promoter for expressing the first nucleic acid sequence as a first transcript and a second promoter for expressing the second nucleic acid sequence as a second transcript. The first transcript will then be translated to a heavy chain polypeptide and the second transcript will be translated into the light chain polypeptide and the resulting antibody will be generated by said heavy and light chain polypeptides. In such an expression vector, the first and second promoters may be same or different in embodiments of the invention. In such an expression vector, a preferred embodiment involves the use of two CMV promoters, i.e. one for each of the first and second nucleic acid sequences encoding the heavy and light chains of an antibody.

In an embodiment of the expression vector, an intron sequence in the 5' untranslated region is included after the promoter(s) to increase export of transcribed mRNA to the cytoplasm from the nucleus of the host cell; moreover, one or more 3' polyadenylation signal sequences may also be included in the expression vector to maximize mRNA levels. Some examples of polyadenylation signal sequences which may be included in the expression vector are SV40 late or early polyadenylation signal sequences and the bovine growth hormone polyadenylation sequence.

In the present invention, a metabolic selection marker such as the gene encoding dihydrofolate reductase (DHFR) may be used as selection marker in an expression vector which is to be transfected into CHO-DG44 cells. The DNA construct can be amplified with the use of Methotrexate (MTX), a DHFR inhibitor.

An alternative marker is the gene encoding Glutamine synthase (GS) which may be used as selection marker in an expression vector to be transfected into CHO GS$^{-/-}$ cells. GS catalyzes the conversion of ammonia and glutamate into glutamine, and MSX inhibits the activity of the GS protein.

An origin of replication which may be used in the present invention may be selected from a pUC origin, a pBR 322 origin; a pACYC origin, a pSC101 origin and a ColE1 origin. However, derivatives of these origins of replication as well as other origins of replication used in the art may also be used. An example of an eukaryotic origin of replication which may be used is an SV40 origin of replication.

The antibiotic resistance marker comprises a gene whose product confers resistance to an antibiotic such as chloramphenicol, ampicillin, zeocin, bleomycin, gentamycin, streptomycin, tetracycline, kanamycin and neomycin. Some examples of antibiotic resistance marker used in the expression vector are therefore a chloramphenicol resistance gene, kanamycin resistance gene, ampicillin resistance gene, zeocin resistance gene, bleomycin resistance gene, gentamycin resistance gene, gentamycin resistance gene, streptomycin resistance gene, tetracycline resistance gene and neomycin resistance gene. The use of these antibiotic resistance markers in expression vectors is known in the art, see e.g. Li F. et al [13] and U.S. Pat. No. 8,138,324.

Other antibiotic selection markers which may be used are Puromycin acetyltransferase, Blasticidin deaminase, Histidinol dehydrogenase, Hygromycin phosphotransferase, Zeocin resistance gene, Bleomycin resistance gene and Aminoglycoside phosphotransferase. These markers use Puromycin, Blasticidin, Histidinol, Hygromycin, Zeocin, Bleomycin and Neomycin (G418), respectively, as selective reagents.

The expression vector may also include one or more transcription termination regions. The transcription termination region is typically downstream of the coding sequence to provide for efficient transcription termination.

In a specific embodiment of the invention for use in the expression of heavy and light chains of an antibody, the expression vector of the present invention comprises the following nucleic acid elements which are also indicated in chapter "Cell line development" in Li F. et al [13]:
  first and second nucleic acid sequences encoding the heavy and light chains of an antibody to be expressed;
  two CMV promoters, i.e. one for each of first and second nucleic acid sequences encoding the heavy and light chains of the antibody;
  an intron sequence in the 5' untranslated region is included after each of the CMV promoters;
  3' polyadenylation signal sequence is included after each of said 5' untranslated regions;
  gene encoding selection marker DHFR;
  DNA construct comprising a TIS sequence (i.e. Kozak sequence) and a signal peptide in front of (i.e. upstream) each of the first and second nucleic acid sequences encoding the heavy and light chains of an antibody; and
  antibiotic resistance marker.

The above disclosed DNA constructs may also be included in an expression cassette suitable for transfecting into mammalian cells. Such an expression cassette may comprise the following nucleic acid elements:
  promoter,
  terminator, and
  selection marker.

The host cell lines used in the present invention may be developed as explained in Li F. et al [13] and Noh S. H. et al [14]. The host cell which hosts the above described embodiments of the expression vector and expression cassette is preferably a mammalian host cell derived from human, hamster or murine cell lines. In preferred embodiments of the invention, CHO cells such as CHO-DG44 cell or a CHO GS$^{-/-}$ cell may be used.

As already discussed above, the various embodiments of DNA constructs, expression vectors, host cells and methods can be used for expressing a recombinant protein or one or more polypeptide chains thereof. An example of a protein which may be expressed is an antibody, antibody fragment, enzyme and hormone.

It is to be noted that, in the present invention, the singular forms "a," "and" and "the" include plural references unless the context clearly dictates otherwise. The present invention also contemplates other embodiments "comprising," "consisting of" and "consisting essentially of," the embodiments or elements presented herein, whether explicitly set forth or not.

The present invention has multiple aspects, illustrated in the non-limiting EXAMPLES section. It should be noted that, in the EXAMPLES section, DNA constructs encoding the heavy and lights chains of Nivolumab (Opdivo®) have been cloned into an expression vector comprising TIS$^{CON}$ and an expression vector comprising TIS$^{EVO}$.

It should be understood that these examples relating to Nivolumab, while indicating preferred embodiments of the invention, are given by way of illustration only. From the above disclosed embodiments of the invention and the following examples, one skilled in the art can ascertain the essential characteristics of this invention, and without departing from the spirit and scope thereof, can make various changes and modifications of the invention to adapt it to various types of therapeutic antibodies (such as mAbs or fragments thereof) and immunoglobins (i.e. IgG, IgM, IgD, IgA and IgE). Thus, various modifications of the invention in addition to those shown and described herein will be apparent to those skilled in the art from the foregoing description. Such modifications are also intended to fall within the scope of the appended claims.

EXAMPLES

Examples 1 and 3 described below show that by introducing the TIS$^{EVO}$ of SEQ ID No 1 into an expression vector, the likelihood of identifying high mAb (Nivolumab) producing mini pools increased compared to mini pools transfected with the TIS$^{CON}$.

Unexpectedly, among the monoclonal cell lines producing >4.2 g/L mAb, ten out of fourteen harboured the TIS$^{EVO}$. In addition, the top ten TIS$^{EVO}$ cell lines yielded on average 0.56 g/L more mAb (Nivolumab) compared to the top ten cell lines with the commonly used TIS$^{CON}$ whilst the quality and biosimilarity were maintained. The present invention underlines the importance and the implications of the TIS sequence during CHO cell line development.

Moreover, Example 2 shows similar post translation modifications for Nivolumab expressed by TIS$^{EVO}$ when compared to Opdivo® (i.e. originator Nivolumab) expressed in an expression vector system not comprising any one of TIS$^{EVO}$ and TIS$^{CON}$. This clearly shows that that quality and biosimilarity of Nivolumab was maintained when TIS$^{EVO}$ was used.

For experimental details pertaining to the examples below, the reader is directed to the separate MATERIALS AND METHODS section. All publications, patent applications, patents and other references mentioned in this document are incorporated by reference in their entirety.

The EXAMPLES and MATERIALS AND METHODS sections disclosed herein are illustrative only and not intended to be limiting.

Example 1—TIS$^{EVO}$ Increases mAb Yield in Fed-Batch Cultivation of Mini Pools In order to compare implications of TIS sequence variants during cell line development in CHO-DG44, nucleotide changes were introduced to the expression vector by altering the TIS sequence GCCACCATGGA (TIS$^{CON}$) to novel TIS sequence of TCGGTCATGGC (TIS$^{EVO}$).

Figure 1:
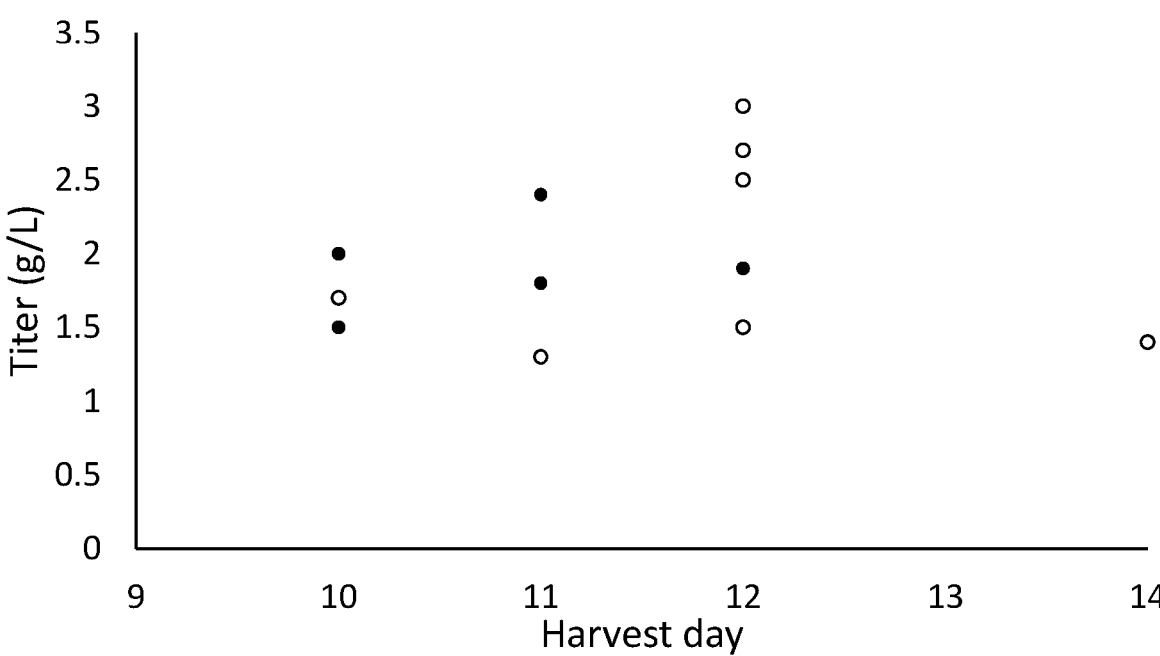
FIG. 1—Increased likelihood of identifying high antibody producing cell cultures for mini-pools containing a TIS$^{EVO}$- chart represents titer values (g/L) on harvest day for mini-pools containing a TIS$^{CON}$ (black) or TIS$^{EVO}$ (hallow).

In parallel experiments, cells were transfected via electroporation with either the TIS$^{EVO}$ or the TIS$^{CON}$ vectors (i.e. vectors comprising TIS$^{EVO}$ or the TIS$^{CON}$ sequences) and integrates were selected for by seeding 4000-8000 viable cells/well in 96-well plates 24 hours after transfection. After screening for the best growing colonies, titers were measured in static cultures and top mini pools were expanded and re-adapted to suspension. Top twelve mini pools based on cell specific productivity (pg/cell/pay) and overall titer (g/L) were further evaluated in a fed batch study in shake flasks. Notably, seven out of the top twelve mini pools were cells transfected with the TIS$^{EVO}$. Moreover, when analysing data from the fed batch study, we saw clear indications of higher titer and cell specific productivity, in addition to increased colony formation in 96-well plates, for mini-pools containing a TIS$^{EVO}$ The fed batch results showed that the top three high producing mini pools had integrated vectors with the TIS$^{EVO}$ (FIGS. 1 and 2). The average max viable cell density (VCD)/ml was lower for mini pools with a TIS$^{EVO}$ ($15.2*10^6$ cells/ml) compared to TIS$^{CON}$ ($20.1*10^6$ cells/ml) (data not shown) and there was prolonged viability for TIS$^{EVO}$ integrates (FIGS. 1 and 2, x-axis). These results suggest that a mRNA with a TIS$^{EVO}$ promote longevity, potentially through recruiting ribosomes more efficiently, thereby enhancing cell specific productivity and titer but slightly hampering VCD (less ribosomes available for rapid growth).

Example 2—Comparable mAb Glycan Profile and Charge Distribution for TIS$^{EVO}$ and TIS$^{CON}$ Mini Pools To assess if the increase in productivity and titer for cells transfected with TIS$^{EVO}$ affects protein quality, mini pools were analysed for charge distribution of acidic and basic species (FIGS. 8 and 9), glycan profiling (FIGS. 5-7) and size distribution, i.e. post translational modifications, PTMs. The resulting data from Water RapiFluor-MS workflow, as illustrated in FIG. 5-9, showed similar PTM patterns and charge distribution for Nivolumab expressed by expression vector systems comprising TIS$^{EVO}$ and TIS$^{CON}$, respectively, when compared to Opdivo® (i.e. originator mAb) expressed in an expression vector system not comprising any one of TIS$^{EVO}$ and TIS$^{CON}$. This clearly indicates that the alteration in translation initiation rates did neither affect protein quality nor biosimilarity.

The glycans which are disclosed in FIGS. 5-8 have the following Oxford Notation names [18]:
A2;
F(6)A2 (same as FA2 in reference 20);
A2[3]G1;
A2[6]G1;
F(6)A2[3]G1 (same as FA2[3]G1 in reference 20);
F(6)A2[6]G1 (same as FA2[6]G1 in reference 20);
F(6)A2G2 (same as FA2G2 in reference 20)
M5; and
F(6)A1.
Increased mAb Production in Monoclonal Cell Lines Harbouring a TIS$^{EVO}$ To generate monoclonal cell lines, top eight mini pools (based on titer and protein quality) were seeded as single cells using fluorescence-activated cell sorting (FACS) and single cell images were taken as a further assurance of monoclonality. The top 48 clones based on monoclonality, cell growth and productivity were expanded and adapted to suspension culture before evaluation in an ambr15 micro-bioreactor run. Cultures were harvested when viability was <70% or on culture day 14 at the latest. When analysing overall yield and cell specific productivity of the mAb producing monoclonal cell lines, we observed a clear difference in titer and specific productivity between the TIS$^{EVO}$ and TIS$^{CON}$ containing cell lines (FIGS. 3 and 4). Among the 48 cultured clones, 14 clones gave rise to accumulated titer values ≥4.2 g/L of which 10 clones harboured a TIS$^{EVO}$. The highest producing cell line also contained a TIS$^{EVO}$ and yielded 6.1 g/L mAb in a generic, non-optimised fed-batch process (FIG. 3). Moreover, when analysing the cell specific productivity 10 out of the 14 high producers contained a TIS$^{EVO}$ with the best TIS$^{EVO}$ variant producing ca. 60 pg/c/d mAb (FIG. 4). Taken together, these results indicate that our rationally designed TIS$^{EVO}$ is superior compared to a standard commonly used TIS$^{CON}$ both in terms of the likelihood of identifying high producers during mini pool generation as well as identifying a monoclonal DG44 cell lines with enhanced productivity and titer.

Materials and Methods

Vector Engineering and Transfection

The expression vectors (i.e. the TIS$^{CON}$ vector and TIS$^{EVO}$ vector) for comparing the TIS$^{CON}$ and TIS$^{EVO}$ both comprised the following nucleic acid elements which are disclosed in the chapter "Cell line development" in Li F. et al [13]:

first and second nucleic acid sequences encoding the heavy and light chains of the antibody to be expressed;

two CMV promoters, i.e. one for each of first and second nucleic acid sequences encoding the heavy and light chains of the antibody;

an intron sequence in the 5' untranslated region is included after each of the CMV promoters;

3' polyadenylation (polyA) signal sequence is included after each of said 5' untranslated regions;

gene encoding selection marker DHFR;

a nucleic acid sequence encoding a signal peptide in front of (i.e. upstream) each of the first and second nucleic acid sequences encoding the heavy and light chains of the antibody to be expressed;

TIS sequences (i.e. Kozak sequences) upstream of the signal peptide nucleic acid sequences; and antibiotic resistance marker.

The first and second nucleic acid sequences encoding the heavy and lights chains of Nivolumab (Opdivo®) were each cloned into an expression vector comprising, either two TIS$^{CON}$ sequences, or two TIS$^{EVO}$ sequences, as described in below paragraphs. The first nucleic acid sequence encoding the heavy chains of Nivolumab comprises a sequence of SEQ ID No 4 while the second nucleic acid sequence encoding the light chains of Nivolumab comprises a sequence of SEQ ID No 6. Thus, the first nucleic acid sequence encodes heavy chains comprising an amino acid sequence of SEQ ID No 5 while the second nucleic acid sequence encodes light chains comprising an amino acid sequence of SEQ ID No 7.

In the vector comprising the two TIS$^{CON}$ sequences (i.e. the TIS$^{CON}$ vector), the nucleic acid sequence encoding each of the signal peptides comprised a nucleic acid sequence for expressing a signal peptide of amino acid sequence MDLLHKNMKHLWFFLLLVAAPRWVLS. This signal peptide has previously been disclosed in Haryadi R. et al [12] and U.S. Pat. No. 10,066,019 for expressing a polypeptide chain of therapeutic antibodies.

For designing the TIS$^{EVO}$ sequence, the GCCACC sequence of the TIS$^{CON}$ sequence was altered to the TCGGTC sequence. In addition, the first codon downstream of the ATG start codon, coding for the first amino acid of the signal peptide, was changed from GAT to GCT resulting in an amino acid substitution at that position. These combinatory changes yielded the TIS$^{EVO}$ sequence comprising the TCGGTCATGGC nucleotide sequence (SEQ ID No 1).

The expression vector comprising the two TIS$^{EVO}$ sequence (SEQ ID No 1) was engineered to comprise two nucleic acid sequences each encoding the signal peptide comprising a nucleic acid sequence of SEQ ID No 2. The nucleic acid sequences of SEQ ID No 1 each comprised:

the ATG start codon in a sequence of SEQ ID No 2; and the first two nucleotides downstream of the ATG start codon in a nucleic acid sequence of SEQ ID No 2.

The nucleic acid sequence of SEQ ID No 2 encodes a novel signal peptide of amino acid sequence MALLHKNMKHLWFFLLLVAAPRWVLS (SEQ ID No 3) which has previously not been disclosed in any prior art documents.

For testing the activity of TIS$^{EVO}$, DNA constructs comprising nucleic acid sequences of SEQ ID No 8 and SEQ ID No 9 encoding heavy chain and light chain of Nivolumab, respectively, were cloned into the expression vector. The DNA constructs used for this purpose comprised nucleic acid sequences of SEQ ID No 12 and SEQ ID No 13 which comprise (i) nucleic acid sequences of SEQ ID No 8 and SEQ ID No 9 encoding heavy and light chain of an antibody, respectively, and (ii) restriction sites which enabled cloning into the expression vector.

Consequently, the DNA constructs comprising the nucleic acid sequences of SEQ ID No 8 and SEQ ID No 12, each comprised:

a first nucleic acid sequence comprising a nucleic acid sequence of SEQ ID No 1 (TIS$^{EVO}$).

a first nucleic acid sequence which encodes a signal peptide comprising a nucleic acid sequence of SEQ ID No 2; and a first nucleic acid sequence which encodes a heavy chain of an antibody comprising a nucleic acid sequence of SEQ ID No 4;

wherein said first nucleic acid sequence of SEQ ID No 1 comprised:

the ATG start codon in SEQ ID No 2 of the first nucleic acid sequence which encodes a signal peptide; and the first two nucleotides downstream of said ATG start codon.

Similarly, the DNA constructs comprising the nucleic acid sequence of SEQ ID No 9 and SEQ ID No 13, each comprised:

a second nucleic acid sequence comprising a nucleic acid sequence of SEQ ID No 1 (TIS$^{EVO}$);

a second nucleic acid sequence which encodes a signal peptide comprising a nucleic acid sequence of SEQ ID No 2; and a second nucleic acid sequence which encodes a light chain of an antibody comprising a nucleic acid sequence of SEQ ID No 6;

wherein said second nucleic acid sequences of SEQ ID No 1 comprised:

the ATG start codon in SEQ ID No 2 of the second nucleic acid sequence which encodes a signal peptide; and the first two nucleotides downstream of said ATG start codon.

For testing the activity of TIS$^{CON}$, two DNA constructs comprising nucleic acid sequences encoding heavy chain (SEQ ID No 4) and light chain (SEQ ID No 6) of Nivolumab, respectively, were cloned into the expression vector. In analogy to the above described vector for testing TIS$^{EVO}$, each of the nucleic acid sequences encoding heavy chain (SEQ ID No 4) and light chain (SEQ ID No 6) of Nivolumab were operably linked to the nucleic acid sequence expressing the signal peptide MDLLHKNMKHLWFFLLLVAAPRWVLS. Each of the nucleic acid sequences expressing said signal peptide were operably linked to the TIS sequence of GCCACC.

Consequently, the TIS$^{CON}$ vector and the TIS$^{EVO}$ vector differed only in that (in which differences in nucleic acid and amino acid sequences have been underlined):

the TIS$^{CON}$ vector comprised two TIS$^{CON}$ sequences of GCCACCATGGA while the TIS$^{EVO}$ vector comprised two TIS$^{EVO}$ sequences of TCGGTCATGGC; and

the TIS$^{CON}$ vector comprised two nucleic acid sequences each expressing a signal peptide of amino acid sequence MDLLHKNMKHLWFFLLLVAAPRWVLS while the TIS$^{EVO}$ vector comprised two nucleic acid sequences each expressing a signal peptide of amino acid sequence MALLHKNMKHLWFFLLLVAAPRWVLS.

Fed-Batch Cultivation for Mini Pool and Clone Evaluation

Standard fed-batch processes were run according to a generic process for mini pool and clone evaluation. Cells were inoculated at a density of $3 \times 10^5$ cells/mL in 25 mL chemically defined production medium using 125 mL shake flasks (mini pools) or in an ambr15 micro bioreactor (clones). Feed A, feed B and glucose were added according to a standard feeding regimen. Cultures were controlled for cell density, viability, product concentration, glucose and lactate. Cells were cultivated for up to 14 days or until viability dropped below 70%.

REFERENCES

1. Noh, S. M., Shin, S. and Lee, G. M. (2020). Cell Line Development for Therapeutic Protein Production. In Cell Culture Engineering (eds G. M. Lee, H. Faustrup Kildegaard, S. Y. Lee, J. Nielsen and G. Stephanopoulos)
2. Lynch, M., & Marinov, G. K. (2015). The bioenergetic costs of a gene. Proceedings of the National Academy of Sciences of the United States of America, 112 (51), 15690-15695.
3. Shah, P., Ding, Y., Niemczyk, M., Kudla, G., & Plotkin, J. B. (2013). Rate-limiting steps in yeast protein translation. Cell, 153 (7), 1589-1601.
4. Kozak M. (1986) Point mutations define a sequence flanking the AUG initiator codon that modulates translation by eukaryotic ribosomes. Cell, 44 (2), 283-92.
5. Svidritskiy, E., Brilot, A. F., Koh, C. S., Grigorieff, N., & Korostelev, A. A. (2014). Structures of yeast 80S ribosome-tRNA complexes in the rotated and nonrotated conformations. Structure (London, England: 1993), 22 (8), 1210-1218.
6. Acevedo, J. M., Hoermann, B., Schlimbach, T., & Teleman, A. A. (2018). Changes in global translation elongation or initiation rates shape the proteome via the Kozak sequence. Scientific reports, 8 (1), 4018.
7. Kozak M. (1987). An analysis of 5'-noncoding sequences from 699 vertebrate messenger RNAs. Nucleic acids research, 15 (20), 8125-8148.
8. Kallehauge, T. B. et al. (2017) Ribosome profiling-guided depletion of an mRNA increases cell growth rate and protein secretion. Sci. Rep. 7, 40388
9. Noderer, W. L., Flockhart, R. J., Bhaduri, A., Diaz de Arce, A. J., Zhang, J., Khavari, P. A., & Wang, C. L. (2014). Quantitative analysis of mammalian translation initiation sites by FACS-seq. Molecular systems biology, 10 (8), 748.
10. Petersen, S. D., Zhang, J., Lee, J. S., Jakociunas, T., Grav, L. M., Kildegaard, H. F., Keasling, J. D., & Jensen, M. K. (2018). Modular 5'-UTR hexamers for context-independent tuning of protein expression in eukaryotes. Nucleic acids research, 46 (21)
11. Kober, L., Zehe, C. and Bode, J. (2013), Optimized signal peptides for the development of high expressing CHO cell lines. Biotechnol. Bioeng., 110:1164-1173
12. Haryadi, R., Ho, S., Kok, Y. J., Pu, H. X., Zheng, L., Pereira, N. A., Li, B., Bi, X., Goh, L. T., Yang, Y., & Song, Z. (2015). Optimization of heavy chain and light chain signal peptides for high level expression of therapeutic antibodies in CHO cells. PloS one, 10 (2), e0116878.
13. Li, F., Vijayasankaran, N., Shen, A. Y., Kiss, R., & Amanullah, A. (2010). Cell culture processes for monoclonal antibody production. mAbs, 2 (5), 466-479.
14. Noh, S. M., Shin, S. and Lee, G. M. (2020). Cell Line Development for Therapeutic Protein Production. In Cell Culture Engineering (eds G. M. Lee, H. Faustrup Kildegaard, S. Y. Lee, J. Nielsen and G. Stephanopoulos).
15. Ramezani, A., Maymand, E. M., Yazdanpanah-Samani, M., Hosseini, A., Toghraie, F. S., & Ghaderi, A. (2017). Improving Pertuzumab production by gene optimization and proper signal peptide selection. Protein expression and purification, 135, 24-32
16. Peng, L., Yu, X., Li, C., Cai, Y., Chen, Y., He, Y., Yang, J., Jin, J., & Li, H. (2016). Enhanced recombinant factor VII expression in Chinese hamster ovary cells by optimizing signal peptides and fed-batch medium. Bioengineered, 7(3), 189-197
17. https://www.ludger.com/docs/info-guides/ludger-igg-glycan-names.pdf

The invention claimed is:

1. A DNA construct for expressing a recombinant protein in mammalian cells, wherein the DNA construct comprises:
    a nucleic acid sequence of SEQ ID No. 1, wherein the nucleic acid sequence of SEQ ID No. 1 is a TIS sequence; and
    a nucleic acid sequence which encodes a signal peptide, wherein the nucleic acid sequence which encodes the signal peptide comprises a nucleic acid sequence of SEQ ID No 2; and wherein the nucleic acid sequence of SEQ ID No. 1 comprises:
    the ATG start codon in the nucleic acid sequence which encodes the first amino acid residue of the signal peptide; and
    the first two nucleotides downstream of the ATG start codon in the nucleic acid sequence which encodes the second amino acid residue of the signal peptide.

2. The DNA construct according to claim 1, wherein the TIS sequence transcribes into an RNA motif that functions as the protein translation initiation site in an mRNA transcript.

3. The DNA construct according to claim 1, wherein the TIS sequence is a Kozak sequence which transcribes into an RNA motif that functions as the protein translation initiation site in an mRNA transcript.

4. The DNA construct according to claim 1, wherein the nucleic acid sequence of SEQ ID. No. 1 comprises:
    6 nucleotides upstream of an ATG start codon; and
    2 nucleotides downstream of an ATG start codon.

5. The DNA construct according to claim 1, wherein the nucleic acid sequence of SEQ ID No. 1 comprises:
    the ATG start codon in SEQ ID No. 2; and
    the first two nucleotides downstream of the ATG start codon in the nucleic acid sequence of SEQ ID No. 2.

6. The DNA construct according to claim 1, wherein the DNA construct comprises a nucleic acid sequence which encodes said recombinant protein, wherein said recombinant protein is an antibody, wherein said antibody is a monoclonal antibody, a polyclonal antibody, a chimeric antibody or a fragment of said antibody.

7. The DNA construct according to claim 6, wherein the DNA construct which comprises the nucleic acid sequence which encodes said recombinant protein is an IgG4 monoclonal antibody.

8. The DNA construct according to claim 1, wherein the nucleic acid sequence which encodes a signal peptide is operably linked to the nucleic acid sequence which encodes the recombinant protein.

9. The DNA construct according to claim 1, wherein the nucleic acid sequence which encodes said recombinant protein comprises:

a first nucleic acid sequence which encodes a heavy chain of an antibody; and a second nucleic acid sequence which encodes a light chain of an antibody.

10. The DNA construct according to claim 9, wherein the nucleic acid sequence which encodes a signal peptide is operably linked to:

a. the first nucleic acid sequence which encodes the heavy chain of an antibody; and/or b. the second nucleic acid sequence which encodes the light chain of an antibody.

11. An expression vector which comprises the DNA construct according to claim 1.

12. An expression cassette comprising the DNA construct according to claim 1.

13. A host cell which comprises a DNA construct according to claim 1, wherein said host cell is a eukaryotic cell.

14. The host cell according to claim 13, wherein said host cell is a mammalian cell.

15. A recombinant protein expressed by a DNA construct according to claim 1, wherein said recombinant protein is an antibody or an antibody fragment thereof, a monoclonal antibody or a fragment thereof.

16. An RNA expressed by the DNA construct according to claim 1.

17. A method of expressing a recombinant protein, comprising the steps of:

a. cloning one or more open reading frames encoding a recombinant protein, or one or more polypeptide chains thereof, into one or more DNA constructs according to claim 1; and b. transfecting the resulting nucleic acid sequences into a host cell, wherein the host cell is a eukaryotic cell.

18. The method according to claim 17, further comprising the step of integrating the transfected nucleic acid sequence into the genome of the host cell.

19. A DNA construct for expressing a signal peptide, wherein the DNA construct comprises a nucleic acid sequence which encodes a signal peptide, wherein the nucleic acid sequence which encodes a signal peptide comprises a nucleic acid sequence of SEQ ID No. 2.

20. An expression vector which comprises the DNA construct according to claim 19.

21. An expression cassette comprising the DNA construct according to claim 19.

22. A host cell which comprises a DNA construct according to claim 19.

23. An RNA expressed by the DNA construct according to claim 19.

24. The recombinant protein according to claim 15, wherein said monoclonal antibody is an IgG4 monoclonal antibody or fragment thereof.

25. The method according to claim 17, wherein said eukaryotic cell is a mammalian cell.

* * * * *

SEQUENCE LISTING

```
<160> NUMBER OF SEQ ID NOS: 14

<210> SEQ ID NO 1
<211> LENGTH: 11
<212> TYPE: DNA
<213> ORGANISM: Artificial Sequence
<220> FEATURE:
<223> OTHER INFORMATION: Kozak sequence - DNA

<400> SEQUENCE: 1
tcggtcatgg c                                                          11

<210> SEQ ID NO 2
<211> LENGTH: 78
<212> TYPE: DNA
<213> ORGANISM: Artificial Sequence
<220> FEATURE:
<223> OTHER INFORMATION: Signal peptide - DNA sequence

<400> SEQUENCE: 2
```

-continued

```
atggctctgc tgcacaagaa catgaagcac ctgtggttct ttctgctgct ggtggccgct      60
cctagatggg tgctgtct                                                    78

<210> SEQ ID NO 3
<211> LENGTH: 26
<212> TYPE: PRT
<213> ORGANISM: Artificial Sequence
<220> FEATURE:
<223> OTHER INFORMATION: Signal peptide aa sequence

<400> SEQUENCE: 3

Met Ala Leu Leu His Lys Asn Met Lys His Leu Trp Phe Phe Leu Leu
1               5                   10                  15

Leu Val Ala Ala Pro Arg Trp Val Leu Ser
            20                  25

<210> SEQ ID NO 4
<211> LENGTH: 1326
<212> TYPE: DNA
<213> ORGANISM: Artificial Sequence
<220> FEATURE:
<223> OTHER INFORMATION: Nivolumab - heavy chain - DNA sequence

<400> SEQUENCE: 4
caggtgcagc tggttgaatc tggtggcgga gtggtgcagc ctggcagatc tctgagactg      60
gattgcaagg cctccggcat caccttctcc aactctggca tgcactgggt ccgacaggcc     120
cctggaaaag gactggaatg ggtcgccgtg atttggtacg acggctctaa gcggtactac     180
gccgactccg tgaagggcag attcaccatc tctcgggaca actccaagaa caccctgttt     240
ctgcagatga actccctgag agccgaggac accgccgtgt actactgtgc caccaacgat     300
gattattggg gccagggcac actggtcacc gtgtcctctg cttctaccaa gggaccctct     360
gtgttccctc tggctccttg ctccagatcc acctctgagt ctaccgctgc tctgggctgc     420
ctggtcaagg attactttcc tgagcctgtg accgtgtctt ggaactctgg tgctctgacc     480
tccggcgtgc acacatttcc agctgtgctg cagtcctccg gcctgtactc tctgtcctct     540
gtcgtgaccg tgccttctag ctctctgggc accaagacct acacctgtaa cgtggaccac     600
aagccttcca acaccaaggt ggacaagcgc gtggaatcta gtacggccc tccttgtcct     660 ccatgtcctg ctccagaatt cctcggcgga ccttccgtgt tcctgtttcc tccaaagcct     720
aaggacaccc tgatgatctc tcggacccct gaagtgacct gcgtggtggt ggatgtgtct     780
caagaggacc ccgaggtgca gttcaattgg tacgtggacg gcgtggaagt gcacaacgcc     840
aagaccaagc ctagagagga acagttcaac tccacctaca gagtggtgtc cgtgctgacc     900
gtgctgcacc aggattggct gaacggcaaa gagtacaagt gcaaggtgtc caacaagggc     960
ctgccttcca gcatcgaaaa gaccatctcc aaggctaagg gccagcctcg ggaacctcag    1020
gtttacaccc tgcctccaag ccaagaggaa atgaccaaga accaggtgtc cctgacctgc    1080
ctcgtgaagg gattctaccc ttccgatatc gccgtggaat gggagtccaa tggccagcct    1140
gagaacaact acaagacaac ccctcctgtg ctggactccg acggctcctt ctttctgtat    1200
tcccgcctga ccgtggacaa gtctagatgg caagagggca cagtgttctc ctgctctgtg    1260
atgcacgagg ccctgcacaa ccactacacc cagaagtccc tgtctctgtc cctgggcaaa    1320
tgatag                                                             1326

<210> SEQ ID NO 5
```

```
<211> LENGTH: 440
<212> TYPE: PRT
<213> ORGANISM: Artificial Sequence
<220> FEATURE:
<223> OTHER INFORMATION: Nivolumab - heavy chain - protein sequence

<400> SEQUENCE: 5

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380
```

```
Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440
```

```
<210> SEQ ID NO 6
<211> LENGTH: 648
<212> TYPE: DNA
<213> ORGANISM: Artificial Sequence
<220> FEATURE:
<223> OTHER INFORMATION: Nivolumab - light chain - DNA sequence

<400> SEQUENCE: 6
gagatcgtgc tgacccagtc tcctgccaca ttgtctctga gtcctggcga gagagctacc      60
ctgtcttgca gagcttccca gtccgtgtcc tcctacctgg cctggtatca gcagaaacct     120
ggacaggccc ctcggctgct gatctacgat gcctctaata gagccacagg catccccgcc     180
agattctctg gctctggatc tggcaccgac ttcaccctga ccatctctag cctggaacct     240
gaggacttcg ccgtgtacta ctgccagcag tcctccaact ggcctagaac ctttggccag     300
ggcaccaagg tggaaatcaa gagaaccgtg gctgcccctt ccgtgttcat cttcccacca     360
tctgacgagc agctgaagtc cggcacagct tctgtcgtgt gcctgctgaa caacttctac     420
cctcgggaag ccaaggtgca gtggaaggtg gacaatgccc tgcagtccgg caactcccaa     480
gagtctgtga ccgagcagga ctccaaggac tctacctaca gcctgtcctc cacactgacc     540
ctgtctaagg ccgactacga gaagcacaag gtgtacgcct gtgaagtgac ccaccaggga     600
ctgtctagcc ccgtgaccaa gtctttcaac agaggcgagt gctgatag                  648
```

```
<210> SEQ ID NO 7
<211> LENGTH: 214
<212> TYPE: PRT
<213> ORGANISM: Artificial Sequence
<220> FEATURE:
<223> OTHER INFORMATION: Nivolumab - light chain - protein sequence

<400> SEQUENCE: 7

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 8
<211> LENGTH: 1410
<212> TYPE: DNA
<213> ORGANISM: Artificial Sequence
<220> FEATURE:
<223> OTHER INFORMATION: Kozak - SP - protein heavy chain - DNA

<400> SEQUENCE: 8
tcggtcatgg ccctgctgca caagaacatg aagcacctgt ggttctttct gctgctggtg      60
gccgctccta gatgggtgtt gtctcaggtg cagctggttg aatctggtgg cggagtggtg     120
cagcctggca gatctctgag actggattgc aaggcctccg gcatcacctt ctccaactct     180
ggcatgcact gggtccgaca ggcccctgga aaaggactgg aatgggtcgc cgtgatttgg     240
tacgacggct ctaagcggta ctacgccgac tccgtgaagg gcagattcac catctctcgg     300
gacaactcca gaacaccct gtttctgcag atgaactccc tgagagccga ggacaccgcc     360
gtgtactact gtgccaccaa cgatgattat tggggccagg gcacactggt caccgtgtcc     420
tctgcttcta ccaagggacc ctctgtgttc cctctggctc cttgctccag atccacctct     480
gagtctaccg ctgctctggg ctgcctggtc aaggattact tcctgagcc tgtgaccgtg     540 tcttggaact ctggtgctct gacctccggc gtgcacacat tccagctgt gctgcagtcc     600 tccggcctgt actctctgtc ctctgtcgtg accgtgcctt ctagctctct gggcaccaag     660
acctacacct gtaacgtgga ccacaagcct tccaacacca ggtggacaa gcgcgtggaa     720 tctaagtacg gccctccttg tcctccatgt cctgctccag aattcctcgg cggaccttcc     780
gtgttcctgt ttcctccaaa gcctaaggac accctgatga tctctcggac ccctgaagtg     840
acctgcgtgg tggtggatgt gtctcaagag gaccccgagg tgcagttcaa ttggtacgtg     900
gacggcgtgg aagtgcacaa cgccaagacc aagcctagag aggaacagtt caactccacc     960
tacagagtgg tgtccgtgct gaccgtgctg caccaggatt ggctgaacgg caaagagtac    1020
aagtgcaagg tgtccaacaa gggcctgcct tccagcatcg aaaagaccat ctccaaggct    1080
aagggccagc tcgggaacc tcaggtttac accctgcctc caagccaaga ggaaatgacc    1140
aagaaccagg tgtccctgac ctgcctcgtg aagggattct accttccga tatcgccgtg    1200 gaatgggagt ccaatggcca gcctgagaac aactacaaga caccccctcc tgtgctggac    1260
tccgacggct ccttcttct gtattcccgc ctgaccgtgg acaagtctag atggcaagag    1320
ggcaacgtgt tctcctgctc tgtgatgcac gaggccctgc acaaccacta cacccagaag    1380
tccctgtctc tgtccctggg caaatgatag                                     1410

<210> SEQ ID NO 9
<211> LENGTH: 732

<212> TYPE: DNA
<213> ORGANISM: Artificial Sequence
<220> FEATURE:
<223> OTHER INFORMATION: Kozak - SP - protein light chain - DNA

<400> SEQUENCE: 9

```
tcggtcatgg ccctgctgca caagaacatg aagcacctgt ggttctttct gctgctggtg        60
gccgctccta gatgggtgct gtctgagatc gtgctgaccc agtctcctgc cacattgtct       120
ctgagtcctg gcgagagagc taccctgtct tgcagagctt cccagtccgt gtcctcctac       180
ctggcctggt atcagcagaa acctggacag gcccctcggc tgctgatcta cgatgcctct       240
aatagagcca caggcatccc cgccagattc tctggctctg gatctggcac cgacttcacc       300
ctgaccatct ctagcctgga acctgaggac ttcgccgtgt actactgcca gcagtcctcc       360
aactggccta gaacctttgg ccagggcacc aaggtggaaa tcaagagaac cgtggctgcc       420
ccttccgtgt tcatcttccc accatctgac gagcagctga gtccggcac agcttctgtc       480 gtgtgcctgc tgaacaactt ctaccctcgg gaagccaagg tgcagtggaa ggtggacaat       540
gccctgcagt ccggcaactc ccaagagtct gtgaccgagc aggactccaa ggactctacc       600
tacagcctgt cctccacact gaccctgtct aaggccgact acgagaagca caaggtgtac       660
gcctgtgaag tgacccacca gggactgtct agccccgtga ccaagtcttt caacagaggc       720
gagtgctgat ag                                                            732
```

<210> SEQ ID NO 10
<211> LENGTH: 466
<212> TYPE: PRT
<213> ORGANISM: Artificial Sequence
<220> FEATURE:
<223> OTHER INFORMATION: SP - protein heavy chain - protein

<400> SEQUENCE: 10

```
Met Ala Leu Leu His Lys Asn Met Lys His Leu Trp Phe Phe Leu Leu
1               5                   10                  15

Leu Val Ala Ala Pro Arg Trp Val Leu Ser Gln Val Gln Leu Val Glu
            20                  25                  30

Ser Gly Gly Gly Val Val Gln Pro Gly Arg Ser Leu Arg Leu Asp Cys
        35                  40                  45

Lys Ala Ser Gly Ile Thr Phe Ser Asn Ser Gly Met His Trp Val Arg
    50                  55                  60

Gln Ala Pro Gly Lys Gly Leu Glu Trp Val Ala Val Ile Trp Tyr Asp
65                  70                  75                  80

Gly Ser Lys Arg Tyr Tyr Ala Asp Ser Val Lys Gly Arg Phe Thr Ile
                85                  90                  95

Ser Arg Asp Asn Ser Lys Asn Thr Leu Phe Leu Gln Met Asn Ser Leu
            100                 105                 110

Arg Ala Glu Asp Thr Ala Val Tyr Tyr Cys Ala Thr Asn Asp Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190
```

-continued

```
Pro Ala Val Leu Gln Ser Ser Gly Leu Tyr Ser Leu Ser Ser Val Val
        195                 200                 205

Thr Val Pro Ser Ser Ser Leu Gly Thr Lys Thr Tyr Thr Cys Asn Val
        210                 215                 220

Asp His Lys Pro Ser Asn Thr Lys Val Asp Lys Arg Val Glu Ser Lys
225                 230                 235                 240

Tyr Gly Pro Pro Cys Pro Pro Cys Pro Ala Pro Glu Phe Leu Gly Gly
                245                 250                 255

Pro Ser Val Phe Leu Phe Pro Pro Lys Pro Lys Asp Thr Leu Met Ile
                260                 265                 270

Ser Arg Thr Pro Glu Val Thr Cys Val Val Val Asp Val Ser Gln Glu
        275                 280                 285

Asp Pro Glu Val Gln Phe Asn Trp Tyr Val Asp Gly Val Glu Val His
        290                 295                 300

Asn Ala Lys Thr Lys Pro Arg Glu Glu Gln Phe Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Gly Leu Pro Ser Ser Ile Glu
                340                 345                 350

Lys Thr Ile Ser Lys Ala Lys Gly Gln Pro Arg Glu Pro Gln Val Tyr
                355                 360                 365

Thr Leu Pro Pro Ser Gln Glu Glu Met Thr Lys Asn Gln Val Ser Leu
        370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Arg Leu Thr Val Asp
                420                 425                 430

Lys Ser Arg Trp Gln Glu Gly Asn Val Phe Ser Cys Ser Val Met His
        435                 440                 445

Glu Ala Leu His Asn His Tyr Thr Gln Lys Ser Leu Ser Leu Ser Leu
        450                 455                 460

Gly Lys
465

<210> SEQ ID NO 11
<211> LENGTH: 240
<212> TYPE: PRT
<213> ORGANISM: Artificial Sequence
<220> FEATURE:
<223> OTHER INFORMATION: SP - protein light chain - protein

<400> SEQUENCE: 11

Met Ala Leu Leu His Lys Asn Met Lys His Leu Trp Phe Phe Leu Leu
1               5                   10                  15

Leu Val Ala Ala Pro Arg Trp Val Leu Ser Glu Ile Val Leu Thr Gln
                20                  25                  30

Ser Pro Ala Thr Leu Ser Leu Ser Pro Gly Glu Arg Ala Thr Leu Ser
        35                  40                  45

Cys Arg Ala Ser Gln Ser Val Ser Ser Tyr Leu Ala Trp Tyr Gln Gln
        50                  55                  60

Lys Pro Gly Gln Ala Pro Arg Leu Leu Ile Tyr Asp Ala Ser Asn Arg
65                  70                  75                  80
```

-continued

```
Ala Thr Gly Ile Pro Ala Arg Phe Ser Gly Ser Gly Ser Gly Thr Asp
                85                  90                  95

Phe Thr Leu Thr Ile Ser Ser Leu Glu Pro Glu Asp Phe Ala Val Tyr
            100                 105                 110

Tyr Cys Gln Gln Ser Ser Asn Trp Pro Arg Thr Phe Gly Gln Gly Thr
            115                 120                 125

Lys Val Glu Ile Lys Arg Thr Val Ala Ala Pro Ser Val Phe Ile Phe
        130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
            195                 200                 205

Lys Ala Asp Tyr Glu Lys His Lys Val Tyr Ala Cys Glu Val Thr His
        210                 215                 220

Gln Gly Leu Ser Ser Pro Val Thr Lys Ser Phe Asn Arg Gly Glu Cys
225                 230                 235                 240

<210> SEQ ID NO 12
<211> LENGTH: 1422
<212> TYPE: DNA
<213> ORGANISM: Artificial Sequence
<220> FEATURE:
<223> OTHER INFORMATION: Restriction site - SP - protein heavy chain -
      DNA

<400> SEQUENCE: 12
ggtacctcgg tcatggccct gctgcacaag aacatgaagc acctgtggtt ctttctgctg      60
ctggtggccg ctcctagatg ggtgttgtct caggtgcagc tggttgaatc tggtggcgga     120
gtggtgcagc ctggcagatc tctgagactg gattgcaagg cctccggcat caccttctcc     180
aactctggca tgcactgggt ccgacaggcc cctggaaaag gactggaatg ggtcgccgtg     240
atttggtacg acggctctaa gcggtactac gccgactccg tgaagggcag attcaccatc     300
tctcgggaca actccaagaa caccctgttt ctgcagatga actccctgag agccgaggac     360
accgccgtgt actactgtgc caccaacgat gattattggg gccagggcac actggtcacc     420
gtgtcctctg cttctaccaa gggaccctct gtgttccctc tggctccttg ctccagatcc     480
acctctgagt ctaccgctgc tctgggctgc ctggtcaagg attactttcc tgagcctgtg     540
accgtgtctt ggaactctgg tgctctgacc tccggcgtgc acacatttcc agctgtgctg     600
cagtcctccg gcctgtactc tctgtcctct gtcgtgaccg tgccttctag ctctctgggc     660
accaagacct acacctgtaa cgtggaccac aagccttcca acaccaaggt ggacaagcgc     720
gtggaatcta gtacggcccc tccttgtcct ccatgtcctg ctccagaatt cctcggcgga     780
ccttccgtgt tcctgtttcc tccaaagcct aaggacaccc tgatgatctc tcggacccct     840
gaagtgacct gcgtggtggt ggatgtgtct caagaggacc ccgaggtgca gttcaattgg     900
tacgtggacg gcgtggaagt gcacaacgcc aagaccaagc ctagagagga acagttcaac     960
tccacctaca gagtggtgtc cgtgctgacc gtgctgcacc aggattggct gaacggcaaa    1020
gagtacaagt gcaaggtgtc caacaagggc ctgccttcca gcatcgaaaa gaccatctcc    1080
aaggctaagg gccagcctcg ggaacctcag gtttacaccc tgcctccaag ccaagaggaa    1140
```

-continued

```
atgaccaaga accaggtgtc cctgacctgc ctcgtgaagg gattctaccc ttccgatatc   1200
gccgtggaat gggagtccaa tggccagcct gagaacaact acaagacaac ccctcctgtg   1260
ctggactccg acggctcctt ctttctgtat tcccgcctga ccgtggacaa gtctagatgg   1320
caagagggca acgtgttctc ctgctctgtg atgcacgagg ccctgcacaa ccactacacc   1380
cagaagtccc tgtctctgtc cctgggcaaa tgatagaagc tt                      1422
```

```
<210> SEQ ID NO 13
<211> LENGTH: 744
<212> TYPE: DNA
<213> ORGANISM: Artificial Sequence
<220> FEATURE:
<223> OTHER INFORMATION: Restriction site - SP - light chain - DNA

<400> SEQUENCE: 13
ggatcctcgg tcatggccct gctgcacaag aacatgaagc acctgtggtt ctttctgctg     60
ctggtggccg ctcctagatg ggtgctgtct gagatcgtgc tgacccagtc tcctgccaca    120
ttgtctctga gtcctggcga gagagctacc ctgtcttgca gagcttccca gtccgtgtcc    180
tcctacctgg cctggtatca gcagaaacct ggacaggccc ctcggctgct gatctacgat    240
gcctctaata gagccacagg catccccgcc agattctctg gctctggatc tggcaccgac    300
ttcaccctga ccatctctag cctggaacct gaggacttcg ccgtgtacta ctgccagcag    360
tcctccaact ggcctagaac ctttggccag ggcaccaagg tggaaatcaa gagaaccgtg    420
gctgcccctt ccgtgttcat cttcccacca tctgacgagc agctgaagtc cggcacagct    480
tctgtcgtgt gcctgctgaa caacttctac cctcgggaag ccaaggtgca gtggaaggtg    540
gacaatgccc tgcagtccgg caactcccaa gagtctgtga ccgagcagga ctccaaggac    600
tctacctaca gcctgtcctc cacactgacc ctgtctaagg ccgactacga gaagcacaag    660
gtgtacgcct gtgaagtgac ccaccaggga ctgtctagcc ccgtgaccaa gtctttcaac    720
agaggcgagt gctgatagct cgag                                          744
```

```
<210> SEQ ID NO 14
<211> LENGTH: 11
<212> TYPE: RNA
<213> ORGANISM: Artificial Sequence
<220> FEATURE:
<223> OTHER INFORMATION: TIS RNA

<400> SEQUENCE: 14
ucggucaugg c                                                         11
```